US010729846B2

(12) United States Patent
Pearce et al.

(10) Patent No.: US 10,729,846 B2
(45) Date of Patent: Aug. 4, 2020

(54) SELF-SEALING PAD FOR A NEEDLE-BASED INFUSION SET

(71) Applicant: C. R. Bard, Inc., Murray Hill, NJ (US)

(72) Inventors: Jeremy A. Pearce, West Jordan, UT (US); Bradley J. VanderStek, West Bountiful, UT (US); Jason R. Stats, Layton, UT (US); William R. Barron, Riverton, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 144 days.

(21) Appl. No.: 16/142,928

(22) Filed: Sep. 26, 2018

(65) Prior Publication Data

US 2019/0022309 A1    Jan. 24, 2019

Related U.S. Application Data

(60) Division of application No. 14/070,246, filed on Nov. 1, 2013, now abandoned, which is a
(Continued)

(51) Int. Cl.
*A61M 5/158* (2006.01)
*A61M 5/32* (2006.01)

(52) U.S. Cl.
CPC ........... *A61M 5/158* (2013.01); *A61M 5/3273* (2013.01); *A61M 5/3275* (2013.01);
(Continued)

(58) Field of Classification Search
CPC .......... A61M 5/158; A61M 2005/1581; A61M 2005/3256; A61M 5/3273;
(Continued)

(56) References Cited

U.S. PATENT DOCUMENTS

| 2,847,995 A | 8/1958 | Adams |
| 2,876,770 A | 3/1959 | White |

(Continued)

FOREIGN PATENT DOCUMENTS

| CN | 1175906 A | 3/1998 |
| CN | 1451028 A | 10/2003 |

(Continued)

OTHER PUBLICATIONS

EP 03257490 filed Nov. 27, 2003 Office Action dated Aug. 9, 2007.
(Continued)

*Primary Examiner* — Matthew F Desanto
(74) *Attorney, Agent, or Firm* — Rutan & Tucker LLP

(57) ABSTRACT

A needle assembly to prevent fluid/vapor escape so as to reduce or prevent fluid exposure to a clinician during use of the needle assembly. The needle assembly may include a handle portion with a needle extending therefrom, and a base portion releasably coupled to the handle portion. The base portion may include a safety assembly to shield a distal tip of the needle and prevent user contact therewith. The base portion may further include a self-sealing pad covering a bottom external surface thereof. The self-sealing pad may include an upper surface designed to mate with the base portion and a raised portion compressively positioned in the opening of the bottom external surface. The needle assembly may further include a fluid isolation component.

15 Claims, 25 Drawing Sheets

Related U.S. Application Data continuation-in-part of application No. 13/229,573, filed on Sep. 9, 2011, now Pat. No. 9,248,234.

(60) Provisional application No. 61/721,412, filed on Nov. 1, 2012, provisional application No. 61/381,762, filed on Sep. 10, 2010.

(52) U.S. Cl.
CPC ............... *A61M 2005/1581* (2013.01); *A61M 2005/325* (2013.01); *A61M 2005/3256* (2013.01)

(58) Field of Classification Search
CPC .......... A61M 2005/325; A61M 5/3275; A61M 2005/1586; A61M 2005/1588; A61M 2025/0266; A61M 2205/60
See application file for complete search history.

(56) References Cited

U.S. PATENT DOCUMENTS

| | | | |
|---|---|---|---|
| 2,925,083 | A | 2/1960 | Craig |
| 3,134,380 | A | 5/1964 | Armao |
| 3,306,290 | A | 2/1967 | Weltman |
| 4,160,450 | A | 7/1979 | Doherty |
| 4,235,234 | A | 11/1980 | Whitney et al. |
| 4,352,254 | A | 10/1982 | Peter et al. |
| 4,352,354 | A | 10/1982 | Ujihara et al. |
| 4,380,234 | A | 4/1983 | Kamen |
| 4,435,175 | A | 3/1984 | Friden |
| 4,564,054 | A | 1/1986 | Gustaysson |
| 4,592,744 | A | 6/1986 | Jagger et al. |
| 4,611,382 | A | 9/1986 | Clark |
| 4,615,468 | A | 10/1986 | Gay |
| 4,627,842 | A | 12/1986 | Katz |
| 4,627,843 | A | 12/1986 | Raines |
| 4,631,058 | A | 12/1986 | Raines |
| 4,632,671 | A | 12/1986 | Dalton |
| 4,645,494 | A | 2/1987 | Lee et al. |
| 4,645,495 | A | 2/1987 | Vaillancourt |
| 4,655,765 | A | 4/1987 | Swift |
| 4,676,782 | A | 6/1987 | Yamamoto et al. |
| 4,676,783 | A | 6/1987 | Jagger et al. |
| 4,676,788 | A | 6/1987 | Vincent |
| 4,695,274 | A | 9/1987 | Fox |
| 4,710,176 | A | 12/1987 | Quick |
| 4,725,267 | A | 2/1988 | Vaillancourt |
| 4,755,173 | A | 7/1988 | Konopka et al. |
| 4,755,369 | A | 7/1988 | Yoshiharu |
| 4,760,847 | A | 8/1988 | Vaillancourt |
| 4,775,369 | A | 10/1988 | Schwartz |
| 4,795,432 | A | 1/1989 | Karczmer |
| 4,813,939 | A | 3/1989 | Marcus |
| 4,820,282 | A | 4/1989 | Hogan |
| D301,742 | S | 6/1989 | Wyzgala et al. |
| 4,846,809 | A | 7/1989 | Sims |
| 4,867,172 | A | 9/1989 | Haber et al. |
| 4,897,083 | A | 1/1990 | Martell |
| 4,935,011 | A | 6/1990 | Hogan |
| 4,935,013 | A | 6/1990 | Haber et al. |
| 4,941,881 | A | 7/1990 | Masters et al. |
| 4,941,882 | A | 7/1990 | Ward et al. |
| 4,944,731 | A | 7/1990 | Cole |
| 4,950,250 | A | 8/1990 | Haber et al. |
| 4,969,876 | A | 11/1990 | Patterson |
| 5,002,533 | A | 3/1991 | Jullien |
| 5,013,305 | A | 5/1991 | Opie et al. |
| 5,053,017 | A | 10/1991 | Chamuel |
| 5,061,250 | A | 10/1991 | Shields |
| 5,070,884 | A | 12/1991 | Columbus et al. |
| 5,085,639 | A | 2/1992 | Ryan |
| 5,088,982 | A | 2/1992 | Ryan |
| 5,092,852 | A | 3/1992 | Poling |
| 5,120,320 | A | 6/1992 | Fayngold |
| 5,176,653 | A | 1/1993 | Metals |
| 5,176,655 | A | 1/1993 | McCormick et al. |
| 5,176,662 | A | 1/1993 | Bartholomew et al. |
| 5,192,275 | A | 3/1993 | Burns |
| 5,197,954 | A | 3/1993 | Cameron |
| 5,236,421 | A | 8/1993 | Becher |
| 5,295,972 | A | 3/1994 | Mischenko |
| 5,312,366 | A | 5/1994 | Vailancourt |
| 5,312,371 | A | 5/1994 | Dombrowski et al. |
| 5,322,517 | A | 6/1994 | Sircom et al. |
| 5,330,438 | A | 7/1994 | Gollobin et al. |
| 5,334,158 | A | 8/1994 | McLees |
| 5,336,187 | A | 8/1994 | Terry et al. |
| 5,336,199 | A | 8/1994 | Castillo et al. |
| 5,342,319 | A | 8/1994 | Watson et al. |
| 5,342,320 | A | 8/1994 | Cameron |
| 5,350,368 | A | 9/1994 | Shields |
| 5,354,281 | A | 10/1994 | Chen et al. |
| 5,419,766 | A | 5/1995 | Chang et al. |
| 5,433,703 | A | 7/1995 | Utterberg et al. |
| 5,451,522 | A | 9/1995 | Queener et al. |
| 5,487,728 | A | 1/1996 | Vaillancourt |
| 5,487,733 | A | 1/1996 | Caizza et al. |
| 5,490,841 | A | 2/1996 | Landis |
| 5,505,711 | A | 4/1996 | Arakawa et al. |
| 5,520,654 | A | 5/1996 | Wahlberg |
| 5,531,704 | A | 7/1996 | Knotek |
| 5,531,713 | A | 7/1996 | Mastronardi et al. |
| 5,554,106 | A | 9/1996 | Layman-Spillar et al. |
| 5,567,495 | A | 10/1996 | Modak et al. |
| 5,569,207 | A | 10/1996 | Gisselberg et al. |
| 5,575,773 | A | 11/1996 | Song et al. |
| 5,584,813 | A | 12/1996 | Livingston et al. |
| 5,584,818 | A | 12/1996 | Morrison |
| 5,607,398 | A | 3/1997 | Parmigiani |
| 5,620,424 | A | 4/1997 | Abramson |
| 5,637,096 | A | 6/1997 | Yoon |
| 5,662,913 | A | 9/1997 | Capelli |
| 5,674,201 | A | 10/1997 | Steinman |
| 5,685,860 | A | 11/1997 | Chang et al. |
| 5,686,096 | A | 11/1997 | Khan et al. |
| 5,693,022 | A | 12/1997 | Haynes |
| 5,695,474 | A | 12/1997 | Daugherty |
| 5,706,520 | A | 1/1998 | Thornton et al. |
| 5,722,959 | A | 3/1998 | Bierman |
| 5,755,694 | A | 5/1998 | Camus et al. |
| 5,762,632 | A | 6/1998 | Whisson |
| 5,779,679 | A | 7/1998 | Shaw |
| 5,817,070 | A | 10/1998 | Tamaro |
| 5,833,665 | A | 11/1998 | Bootman et al. |
| 5,848,990 | A | 12/1998 | Cirelli et al. |
| 5,853,393 | A | 12/1998 | Bogert |
| 5,858,004 | A | 1/1999 | Shields |
| 5,879,330 | A | 3/1999 | Bell |
| 5,885,254 | A | 3/1999 | Matyas |
| 5,885,255 | A | 3/1999 | Jaeger, Jr. et al. |
| 5,951,522 | A | 9/1999 | Rosato et al. |
| 5,951,525 | A | 9/1999 | Thorne et al. |
| 5,993,426 | A | 11/1999 | Hollister |
| 6,042,570 | A | 3/2000 | Bell et al. |
| 6,126,637 | A * | 10/2000 | Kriesel ................. A61M 5/152 604/132 |
| 6,165,156 | A | 12/2000 | Cesarczyk et al. |
| 6,210,373 | B1 | 4/2001 | Allmon |
| 6,238,375 | B1 | 5/2001 | Powell |
| 6,261,264 | B1 | 7/2001 | Tamaro |
| 6,451,003 | B1 | 9/2002 | Prosl et al. |
| 6,497,669 | B1 | 12/2002 | Kensey |
| 6,497,682 | B1 | 12/2002 | Quartararo |
| 6,500,155 | B2 | 12/2002 | Sasso |
| 6,537,255 | B1 | 3/2003 | Raines |
| 6,579,539 | B2 | 6/2003 | Lawson et al. |
| 6,613,015 | B2 | 9/2003 | Sandstrom et al. |
| 6,620,136 | B1 | 9/2003 | Pressly, Sr. et al. |
| 6,623,462 | B2 | 9/2003 | Guzzo et al. |
| 6,629,959 | B2 | 10/2003 | Kuracina et al. |
| 6,659,984 | B2 | 12/2003 | Maclean Crawford et al. |
| 6,663,604 | B1 | 12/2003 | Huet |
| 6,676,633 | B2 | 1/2004 | Smith et al. |

(56) References Cited

U.S. PATENT DOCUMENTS

| | | | |
|---|---|---|---|
| 6,689,102 B2 | 2/2004 | Greene |
| 6,699,217 B2 | 3/2004 | Bennett et al. |
| 6,719,727 B2 | 4/2004 | Brimhall et al. |
| 6,749,588 B1 | 6/2004 | Howell et al. |
| 6,755,805 B1 | 6/2004 | Reid |
| 6,783,002 B1 | 8/2004 | Pavlo |
| 6,808,509 B1 | 10/2004 | Davey |
| 6,824,530 B2 | 11/2004 | Wagner et al. |
| 6,911,020 B2 | 6/2005 | Raines |
| 6,916,310 B2 | 7/2005 | Sommerich |
| 6,918,894 B2 | 7/2005 | Fleury et al. |
| 6,921,388 B2 | 7/2005 | Swenson |
| 6,926,693 B2 | 8/2005 | Enns |
| 6,932,803 B2 | 8/2005 | Newby |
| 6,969,372 B1 | 11/2005 | Halseth |
| 6,972,002 B2 | 12/2005 | Thorne |
| 6,997,902 B2 | 2/2006 | Thorne et al. |
| 7,083,600 B2 | 8/2006 | Meloul |
| 7,147,623 B2 | 12/2006 | Mathiasen |
| 7,150,725 B2 | 12/2006 | Wilkinson |
| 7,214,208 B2 | 5/2007 | Vaillancourt et al. |
| 7,361,159 B2 | 4/2008 | Fiser et al. |
| 7,407,493 B2 | 8/2008 | Cane' |
| 7,438,703 B2 | 10/2008 | Barrus et al. |
| 7,569,044 B2 | 8/2009 | Triplett et al. |
| 7,601,139 B2 | 10/2009 | Woehr et al. |
| 7,604,616 B2 | 10/2009 | Thoresen et al. |
| 7,637,893 B2 | 12/2009 | Christensen et al. |
| 7,662,159 B2 | 2/2010 | Brandigi |
| 7,717,888 B2 | 5/2010 | Vaillancourt et al. |
| 7,776,016 B1 | 8/2010 | Halseth et al. |
| 7,947,021 B2 | 5/2011 | Bourne et al. |
| 7,967,797 B2 | 6/2011 | Winsor et al. |
| 8,066,678 B2 | 11/2011 | Vaillancourt et al. |
| 8,152,768 B2 | 4/2012 | Halseth et al. |
| 8,263,100 B2 | 9/2012 | Areskoug et al. |
| 8,293,965 B2 | 10/2012 | McMaken et al. |
| 8,486,004 B1 | 7/2013 | Propp |
| 8,569,567 B2 | 10/2013 | Ovington |
| 8,574,197 B2 | 11/2013 | Halseth et al. |
| 8,579,863 B2 | 11/2013 | Scherr |
| 8,597,253 B2 | 12/2013 | Vaillancourt |
| 8,708,969 B2 | 4/2014 | Carlyon |
| 8,728,029 B2 | 5/2014 | Vaillancourt et al. |
| 8,852,154 B2 | 10/2014 | Halseth et al. |
| 9,248,234 B2 | 2/2016 | Barron |
| 9,566,417 B1 | 2/2017 | Propp |
| 9,579,451 B2 | 2/2017 | Stumpp |
| 9,713,673 B2 | 7/2017 | Vaillancourt |
| 10,143,799 B2 | 12/2018 | Barron et al. |
| 10,525,234 B2 | 1/2020 | Howell et al. |
| 2001/0025168 A1* | 9/2001 | Gross ............... A61M 5/14248 604/506 |
| 2001/0039401 A1 | 11/2001 | Ferguson et al. |
| 2002/0055711 A1 | 5/2002 | Lavi et al. |
| 2002/0072716 A1 | 6/2002 | Barrus et al. |
| 2002/0099340 A1 | 7/2002 | Crawford et al. |
| 2002/0151852 A1 | 10/2002 | Crawford et al. |
| 2002/0165497 A1 | 11/2002 | Greene |
| 2002/0173749 A1 | 11/2002 | Wagner et al. |
| 2002/0177816 A1 | 11/2002 | Brimhall et al. |
| 2002/0177818 A1 | 11/2002 | Vaillancourt |
| 2002/0183652 A1 | 12/2002 | Kensey |
| 2003/0060774 A1 | 3/2003 | Woehr et al. |
| 2003/0069546 A1 | 4/2003 | Sandstrom et al. |
| 2003/0093101 A1 | 5/2003 | O'Heeron et al. |
| 2003/0097098 A1* | 5/2003 | Lavi ............... A61M 5/158 604/263 |
| 2003/0105430 A1 | 6/2003 | Lavi et al. |
| 2003/0114797 A1 | 6/2003 | Vaillancourt et al. |
| 2003/0144627 A1 | 7/2003 | Woehr et al. |
| 2003/0148994 A1 | 8/2003 | Levinson |
| 2003/0181872 A1 | 9/2003 | Newby |
| 2003/0199827 A1 | 10/2003 | Thorne |
| 2004/0044318 A1 | 3/2004 | Fiser et al. |
| 2004/0049159 A1 | 3/2004 | Barrus et al. |
| 2004/0156908 A1 | 8/2004 | Polaschegg |
| 2004/0225264 A1 | 11/2004 | Bourne et al. |
| 2004/0236288 A1 | 11/2004 | Howell et al. |
| 2005/0027263 A1 | 2/2005 | Woehr et al. |
| 2005/0090784 A1 | 4/2005 | Nielsen et al. |
| 2005/0107743 A1 | 5/2005 | Fangrow |
| 2005/0107748 A1 | 5/2005 | Thorne et al. |
| 2005/0107749 A1 | 5/2005 | Smith et al. |
| 2005/0124938 A1 | 6/2005 | Yang |
| 2005/0137528 A1 | 6/2005 | Wilkinson |
| 2005/0191355 A1 | 9/2005 | Foss |
| 2006/0064061 A1 | 3/2006 | Solomon et al. |
| 2006/0074387 A1 | 4/2006 | Thorne et al. |
| 2006/0155245 A1 | 7/2006 | Woehr |
| 2006/0161116 A1 | 7/2006 | Willis et al. |
| 2006/0182787 A1 | 8/2006 | Jaenichen et al. |
| 2006/0253076 A1 | 11/2006 | Butts et al. |
| 2006/0276836 A1 | 12/2006 | Bergin et al. |
| 2007/0038182 A1 | 2/2007 | Bialecki et al. |
| 2007/0038183 A1 | 2/2007 | Bialecki et al. |
| 2007/0038184 A1 | 2/2007 | Bialecki et al. |
| 2007/0038185 A1 | 2/2007 | Albert et al. |
| 2007/0073221 A1 | 3/2007 | Bialecki et al. |
| 2007/0073222 A1 | 3/2007 | Lilley et al. |
| 2007/0078432 A1 | 4/2007 | Halseth et al. |
| 2007/0191771 A1* | 8/2007 | Moyer ............... A61M 39/02 604/158 |
| 2007/0191772 A1* | 8/2007 | Wojcik ............... A61M 5/158 604/158 |
| 2008/0015481 A1 | 1/2008 | Bergin et al. |
| 2008/0063693 A1 | 3/2008 | Cook et al. |
| 2008/0147003 A1 | 6/2008 | Menzi et al. |
| 2008/0243082 A1 | 10/2008 | Goodman |
| 2008/0262434 A1 | 10/2008 | Vaillancourt |
| 2009/0005743 A1 | 1/2009 | Vaillancourt et al. |
| 2009/0143737 A1 | 6/2009 | Kobayashi et al. |
| 2009/0157000 A1 | 6/2009 | Waller |
| 2009/0254050 A1 | 10/2009 | Bottcher |
| 2009/0281499 A1 | 11/2009 | Harding et al. |
| 2010/0076362 A1 | 3/2010 | Utterberg et al. |
| 2010/0100049 A1 | 4/2010 | Godfrey |
| 2010/0179473 A1 | 7/2010 | Genosar |
| 2010/0312183 A1 | 12/2010 | Halseth et al. |
| 2011/0009831 A1 | 1/2011 | Burkholz et al. |
| 2011/0021997 A1 | 1/2011 | Kyvik et al. |
| 2011/0106014 A1 | 5/2011 | Helm, Jr. |
| 2011/0111012 A1 | 5/2011 | Pepper et al. |
| 2011/0301619 A1 | 12/2011 | Walters |
| 2012/0046612 A1 | 2/2012 | Scheremet et al. |
| 2012/0046621 A1 | 2/2012 | Vaillancourt et al. |
| 2012/0065587 A1 | 3/2012 | Barron et al. |
| 2012/0089069 A1 | 4/2012 | Patel |
| 2012/0130315 A1 | 5/2012 | Weadock et al. |
| 2012/0184922 A1 | 7/2012 | Halseth et al. |
| 2013/0110025 A1 | 5/2013 | Donnellan et al. |
| 2013/0150791 A1 | 6/2013 | Peterson et al. |
| 2013/0150796 A1 | 6/2013 | Souza et al. |
| 2013/0172260 A1 | 7/2013 | Polaschegg |
| 2013/0190724 A1 | 7/2013 | Polaschegg |
| 2013/0274667 A1 | 10/2013 | Conrad-Vlasak et al. |
| 2013/0310764 A1 | 11/2013 | Burkholz et al. |
| 2014/0039416 A1 | 2/2014 | Vaillancourt |
| 2014/0058354 A1 | 2/2014 | Halseth et al. |
| 2014/0066894 A1 | 3/2014 | Pearce et al. |
| 2015/0297867 A1 | 10/2015 | Howell et al. |
| 2019/0160261 A1 | 5/2019 | VanderStek |

FOREIGN PATENT DOCUMENTS

| | | |
|---|---|---|
| CN | 101309714 A | 11/2008 |
| CN | 103497278 A | 1/2014 |
| DE | 3808688 A1 | 1/1989 |
| DE | 3802353 A1 | 8/1989 |
| DE | 20210394 U1 | 9/2002 |
| EP | 0344606 A2 | 12/1989 |
| EP | 451040 A1 | 10/1991 |
| EP | 0747082 A2 | 12/1996 |
| EP | 0763369 A1 | 3/1997 |

(56) References Cited

FOREIGN PATENT DOCUMENTS

| | | |
|---|---|---|
| EP | 1350537 A1 | 10/2003 |
| EP | 1430921 A2 | 6/2004 |
| EP | 2436421 A1 | 4/2012 |
| EP | 2613824 A1 | 7/2013 |
| FR | 2684006 A1 | 5/1993 |
| JP | H03-000077 A | 1/1991 |
| JP | 61-25558 A | 5/1994 |
| JP | 6226919 A | 8/1994 |
| JP | H06-304254 A | 11/1994 |
| JP | 7-148270 A | 6/1995 |
| JP | H07-299142 A | 11/1995 |
| JP | 9099071 A | 4/1997 |
| JP | 2001-218844 A | 8/2001 |
| JP | 2002345955 A | 12/2002 |
| JP | 2003-305128 A | 10/2003 |
| JP | 2004-195227 A | 7/2004 |
| JP | 2007-521918 A | 8/2007 |
| JP | 4355567 | 8/2009 |
| JP | 2010-000300 A | 1/2010 |
| WO | 1988007387 A1 | 10/1988 |
| WO | 1994000172 A1 | 1/1994 |
| WO | 1998006642 | 2/1998 |
| WO | 1999059660 A1 | 11/1999 |
| WO | 2004020033 A1 | 3/2004 |
| WO | 2005049116 A1 | 6/2005 |
| WO | 2006134100 A1 | 12/2006 |
| WO | 2007094898 A2 | 8/2007 |
| WO | 2012034085 A1 | 3/2012 |
| WO | 2012/132774 A1 | 10/2012 |

OTHER PUBLICATIONS

EP 03257490 filed Nov. 27, 2003 Search Report dated Jul. 23, 2004.
EP 15814436.0 filed Jan. 11, 2017 Extended European Search Report dated Feb. 1, 2018.
JP 2003-416415 filed Dec. 15, 2003 Office Action dated Feb. 23, 2007.
JP 2003-416415 filed Dec. 15, 2003 Office Action dated May 30, 2006.
JP 2016-185696 filed Sep. 23, 2016 Office Action dated Jul. 3, 2017.
JP 2016-185696 filed Sep. 23, 2016 Office Action dated Mar. 27, 2018.
JP2013-528355 filed Jan. 25, 2013, First Office Action dated Jun. 23, 2015.
JP2013-528355 filed Jan. 25, 2013, Second Office Action dated May 31, 2016.
PCT/US11/51102 International Preliminary Report on Patentabillity dated Mar. 21, 2013.
PCT/US11/51102 International Search Report and Written Opinion dated Dec. 23, 2011.
PCT/US2015/038853 filed Jul. 1, 2015 International Search Report and Written Opinion dated Oct. 6, 2015.
U.S. Appl. No. 10/320,168, filed Dec. 16, 2002 Advisory Action dated Aug. 22, 2005.
U.S. Appl. No. 10/320,168, filed Dec. 16, 2002 Advisory Action dated Nov. 16, 2005.
U.S. Appl. No. 10/320,168, filed Dec. 16, 2002 Final Office Action dated Jul. 13, 2005.
U.S. Appl. No. 10/320,168, filed Dec. 16, 2002 Non-Final Office Action dated Sep. 3, 2004.
U.S. Appl. No. 10/320,168, filed Dec. 16, 2002 Notice of Allowance dated Aug. 29, 2011.
U.S. Appl. No. 10/320,168, filed Dec. 16, 2002 Notice of Allowance dated May 13, 2011.
U.S. Appl. No. 10/787,605, filed Feb. 26, 2004 Advisory Action dated Jul. 16, 2007.
U.S. Appl. No. 10/787,605, filed Feb. 26, 2004 Final Office Action dated Apr. 4, 2008.
U.S. Appl. No. 10/787,605, filed Feb. 26, 2004 Final Office Action dated Jan. 20, 2010.
U.S. Appl. No. 10/787,605, filed Feb. 26, 2004 Final Office Action dated Jan. 25, 2007.
U.S. Appl. No. 10/787,605, filed Feb. 26, 2004 Non-Final Office Action dated Jul. 28, 2006.
U.S. Appl. No. 10/787,605, filed Feb. 26, 2004 Non-Final Office Action dated Oct. 2, 2008.
U.S. Appl. No. 10/787,605, filed Feb. 26, 2004 Non-Final Office Action dated Sep. 10, 2007.
U.S. Appl. No. 11/788,542, filed Apr. 20, 2007 Decision on Appeal dated Oct. 24, 2012.
U.S. Appl. No. 11/788,542, filed Apr. 20, 2007 Examiners Answer dated Jun. 3, 2010.
U.S. Appl. No. 11/788,542, filed Apr. 20, 2007 Final Office Action dated Dec. 16, 2009.
U.S. Appl. No. 11/788,542, filed Apr. 20, 2007 Non-Final Office Action dated Aug. 27, 2008.
U.S. Appl. No. 11/788,542, filed Apr. 20, 2007 Non-Final Office Action dated Jan. 8, 2009.
U.S. Appl. No. 11/788,542, filed Apr. 20, 2007 Non-Final Office Action dated Jul. 10, 2009.
U.S. Appl. No. 12/221,034, filed Jul. 30, 2008 Final Office Action dated Dec. 8, 2009.
U.S. Appl. No. 12/221,034, filed Jul. 30, 2008 Non-Final Office Action dated Jan. 30, 2009.
U.S. Appl. No. 12/221,034, filed Jul. 30, 2008 Non-Final Office Action dated Jun. 26, 2009.
U.S. Appl. No. 12/221,034, filed Jul. 30, 2008 Notice of Allowance dated Feb. 25, 2010.
U.S. Appl. No. 12/855,605, filed Aug. 12, 2010 Final Office Action dated Oct. 4, 2011.
U.S. Appl. No. 12/855,605, filed Aug. 12, 2010 Non-Final Office Action dated Apr. 27, 2011.
U.S. Appl. No. 12/855,605, filed Aug. 12, 2010 Notice of Allowance dated Dec. 12, 2011.
U.S. Appl. No. 13/229,573, filed Sep. 9, 2011 Advisory Action dated Aug. 5, 2014.
U.S. Appl. No. 13/229,573, filed Sep. 9, 2011 Final Office Action dated Jun. 20, 2014.
U.S. Appl. No. 13/229,573, filed Sep. 9, 2011 Final Office Action dated May 6, 2015.
U.S. Appl. No. 13/229,573, filed Sep. 9, 2011 Non-Final Office Action dated Nov. 27, 2013.
U.S. Appl. No. 13/229,573, filed Sep. 9, 2011 Non-Final Office Action dated Oct. 24, 2014.
U.S. Appl. No. 13/229,573, filed Sep. 9, 2011, Notice of Allowance dated Jul. 15, 2015.
U.S. Appl. No. 13/285,774, filed Oct. 31, 2011 Final Office Action dated Oct. 28, 2013.
U.S. Appl. No. 13/285,774, filed Oct. 31, 2011 Non-Final Office Action dated Dec. 13, 2012.
U.S. Appl. No. 13/285,774, filed Oct. 31, 2011 Non-Final Office Action dated Jul. 3, 2012.
U.S. Appl. No. 13/285,774, filed Oct. 31, 2011 Non-Final Office Action dated Jun. 3, 2013.
U.S. Appl. No. 13/434,368, filed Mar. 29, 2012 Non-Final Office Action dated Mar. 20, 2013.
U.S. Appl. No. 14/045,663, filed Oct. 3, 2013 Advisory Action dated May 12, 2016.
U.S. Appl. No. 14/045,663, filed Oct. 3, 2013 Final Office Action dated Dec. 12, 2016.
U.S. Appl. No. 14/045,663, filed Oct. 3, 2013 Final Office Action dated Feb. 25, 2016.
U.S. Appl. No. 14/045,663, filed Oct. 3, 2013 Non-Final Office Action dated Aug. 13, 2015.
U.S. Appl. No. 14/045,663, filed Oct. 3, 2013 Non-Final Office Action dated Jun. 15, 2016.
U.S. Appl. No. 14/045,663, filed Oct. 3, 2013 Notice of Allowance dated Mar. 15, 2017.
U.S. Appl. No. 14/070,246, filed Nov. 1, 2013 Advisory Action dated Nov. 29, 2016.
U.S. Appl. No. 14/070,246, filed Nov. 1, 2013 Examiner's Answer dated Jun. 23, 2017.

(56) References Cited

OTHER PUBLICATIONS

U.S. Appl. No. 14/070,246, filed Nov. 1, 2013 Final Office Action dated Oct. 21, 2015.
U.S. Appl. No. 14/070,246, filed Nov. 1, 2013 Final Office Action dated Sep. 22, 2016.
U.S. Appl. No. 14/070,246, filed Nov. 1, 2013 Non-Final Office Action dated Apr. 8, 2015.
U.S. Appl. No. 14/070,246, filed Nov. 1, 2013 Non-Final Office Action dated Mar. 14, 2016.
U.S. Appl. No. 14/070,319, filed Nov. 1, 2013 Notice of Allowance dated Jun. 23, 2014.
U.S. Appl. No. 14/789,341, filed Jul. 1, 2015 Non-Final Office Action dated Apr. 20, 2018.
U.S. Appl. No. 14/789,341, filed Jul. 1, 2015 Restriction Requirement dated Nov. 16, 2017.
U.S. Appl. No. 15/012,800, filed Feb. 1, 2016 Notice of Allowance dated Aug. 1, 2018.
U.S. Appl. No. 14/789,341, filed Jul. 1, 2015 Notice of Allowance dated Aug. 21, 2019.
CN 201580039156.3 filed Jan. 18, 2017 Office Action dated Apr. 24, 2019.
U.S. Appl. No. 14/789,341, filed Jul. 1, 2015 Advisory Action dated Feb. 7, 2019.
U.S. Appl. No. 14/789,341, filed Jul. 1, 2015 Final Office Action dated Dec. 31, 2018.

\* cited by examiner

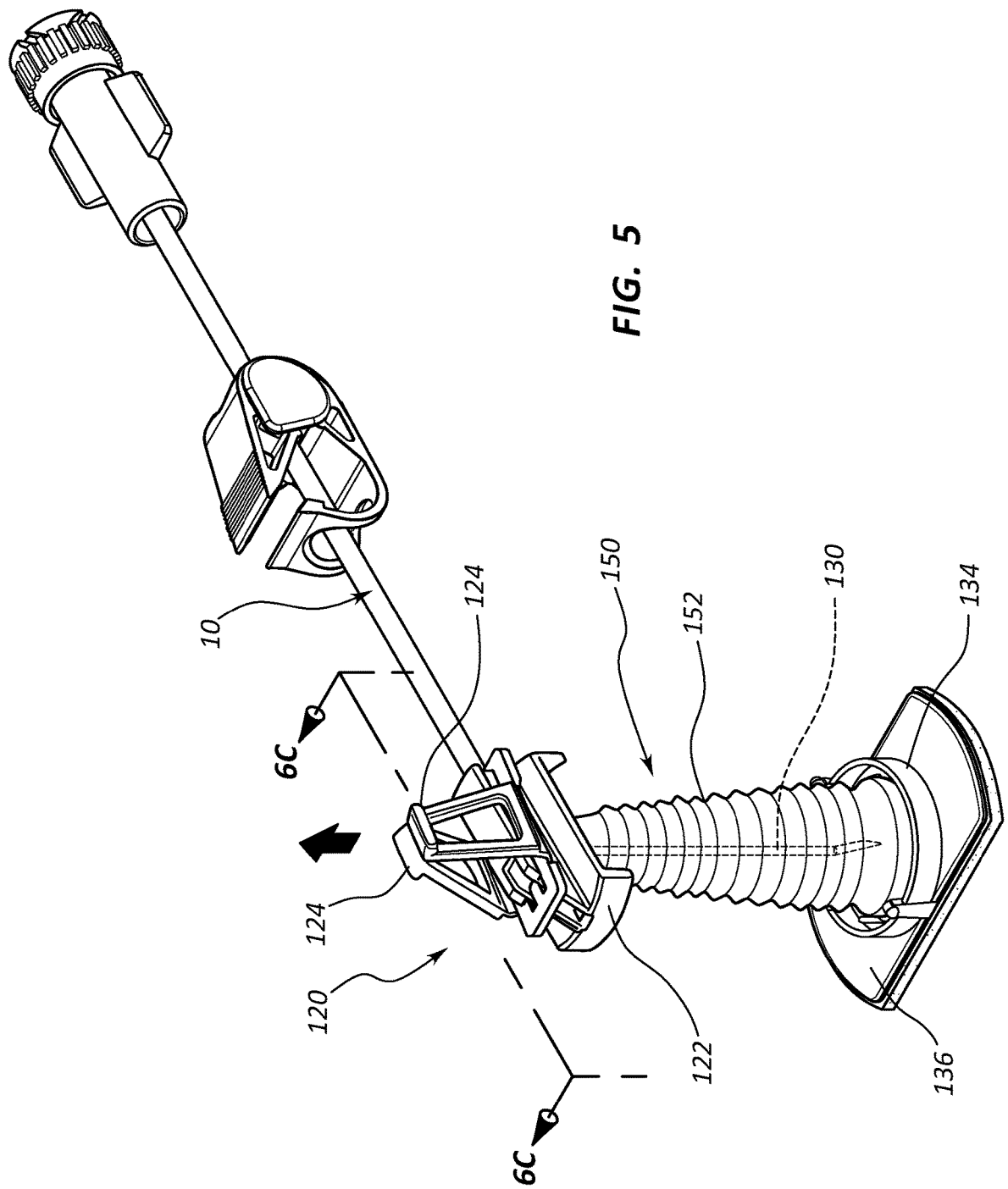

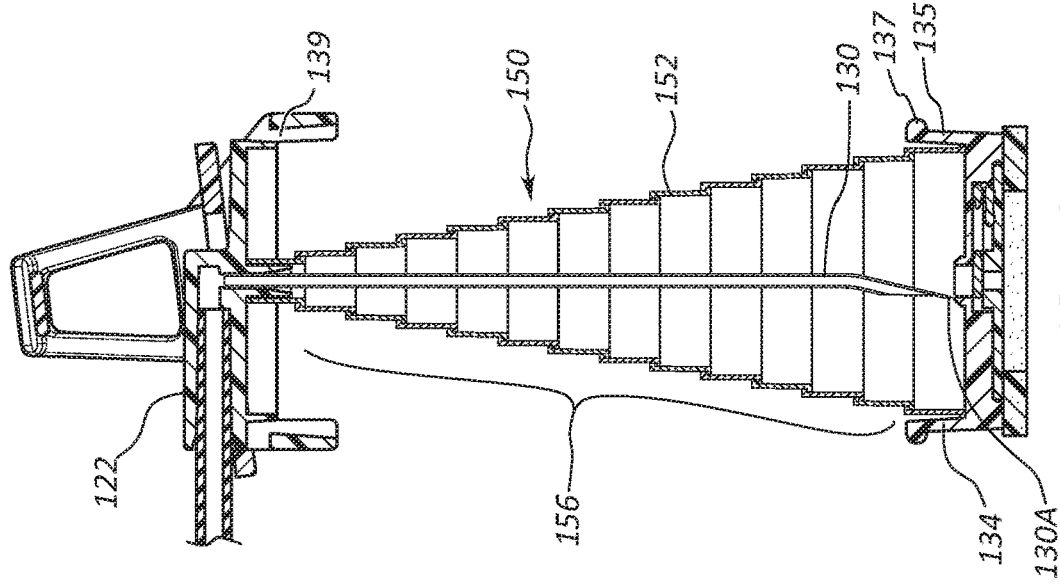
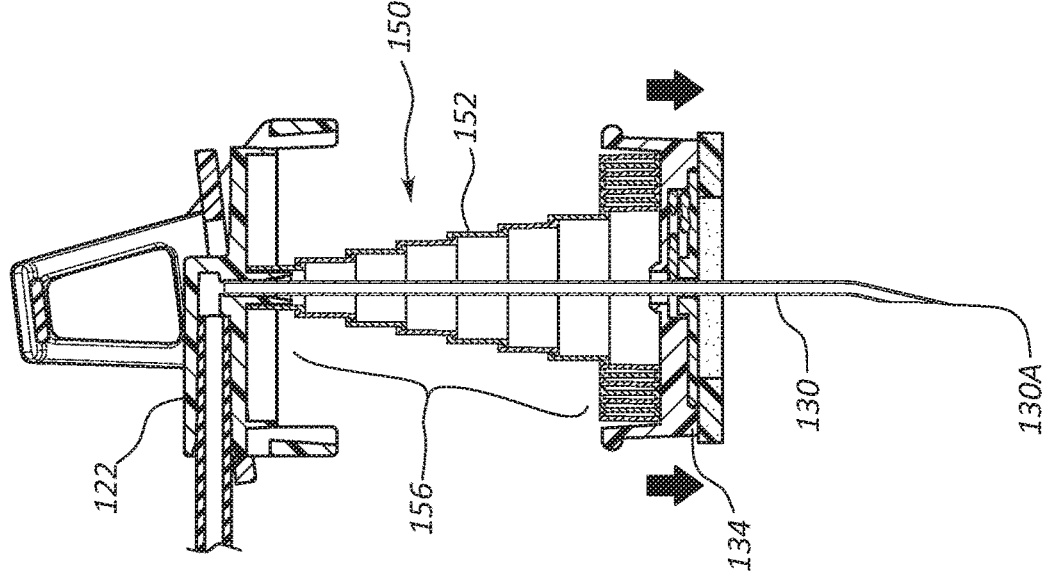
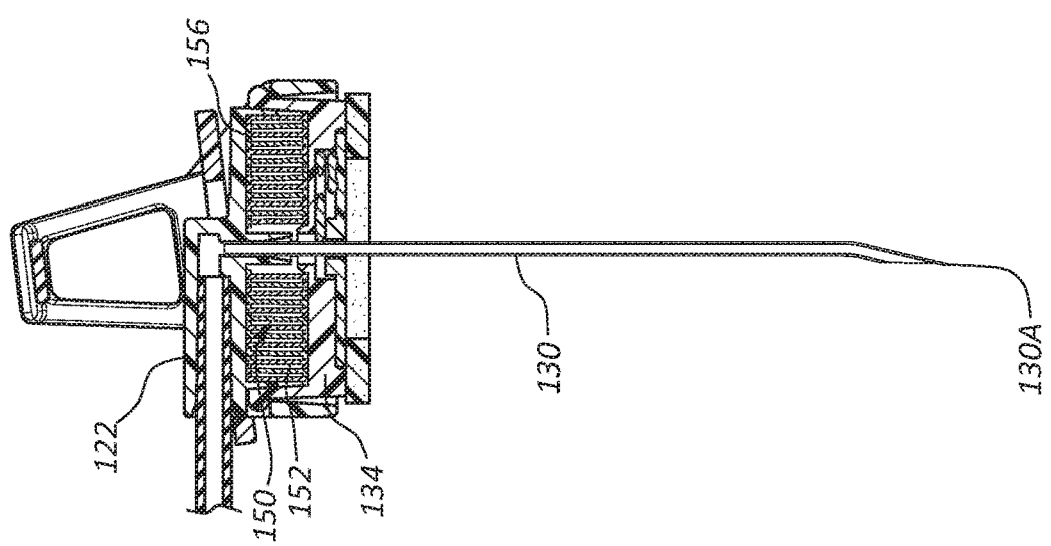

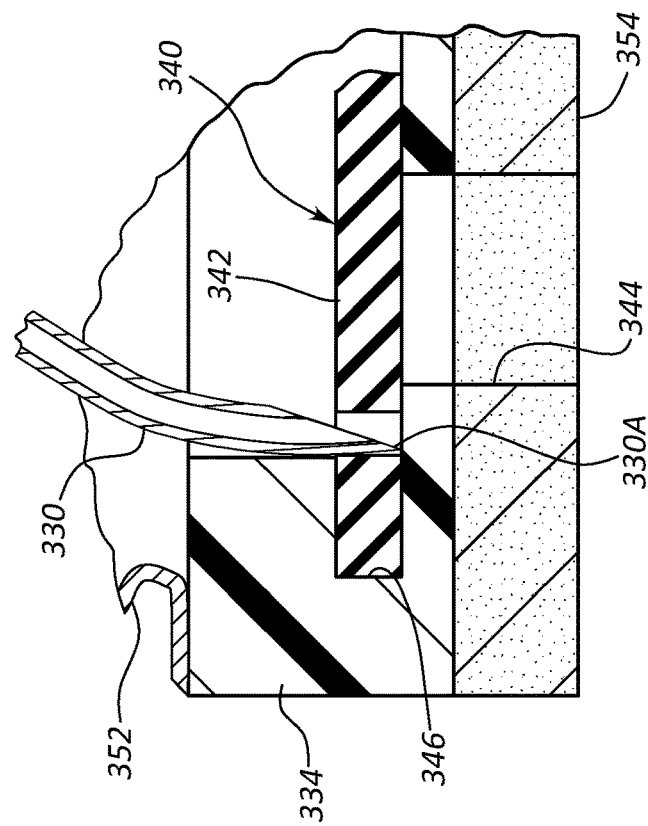
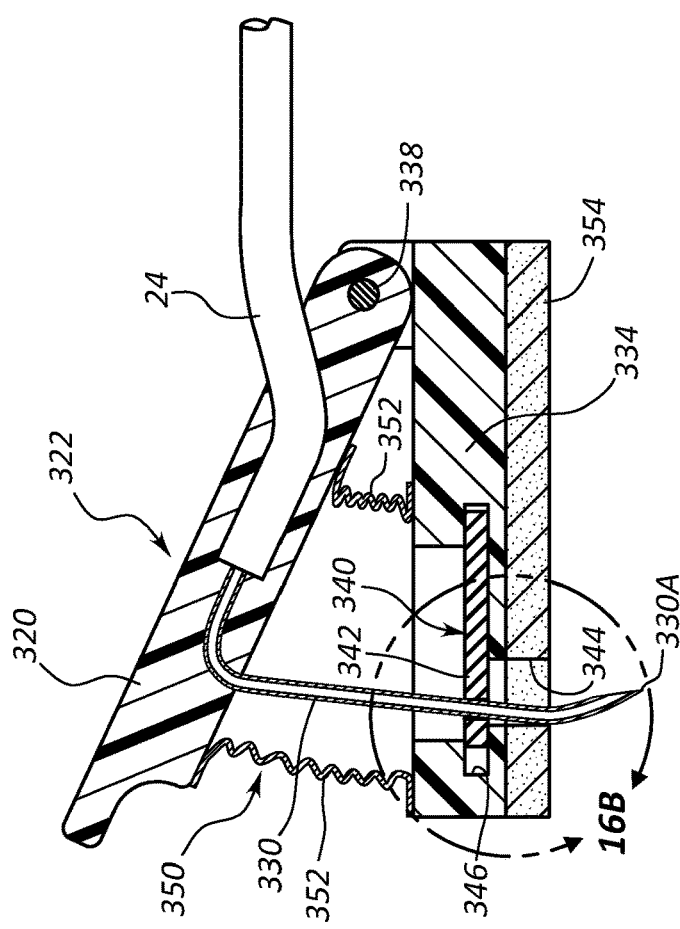
FIG. 16B
FIG. 16A

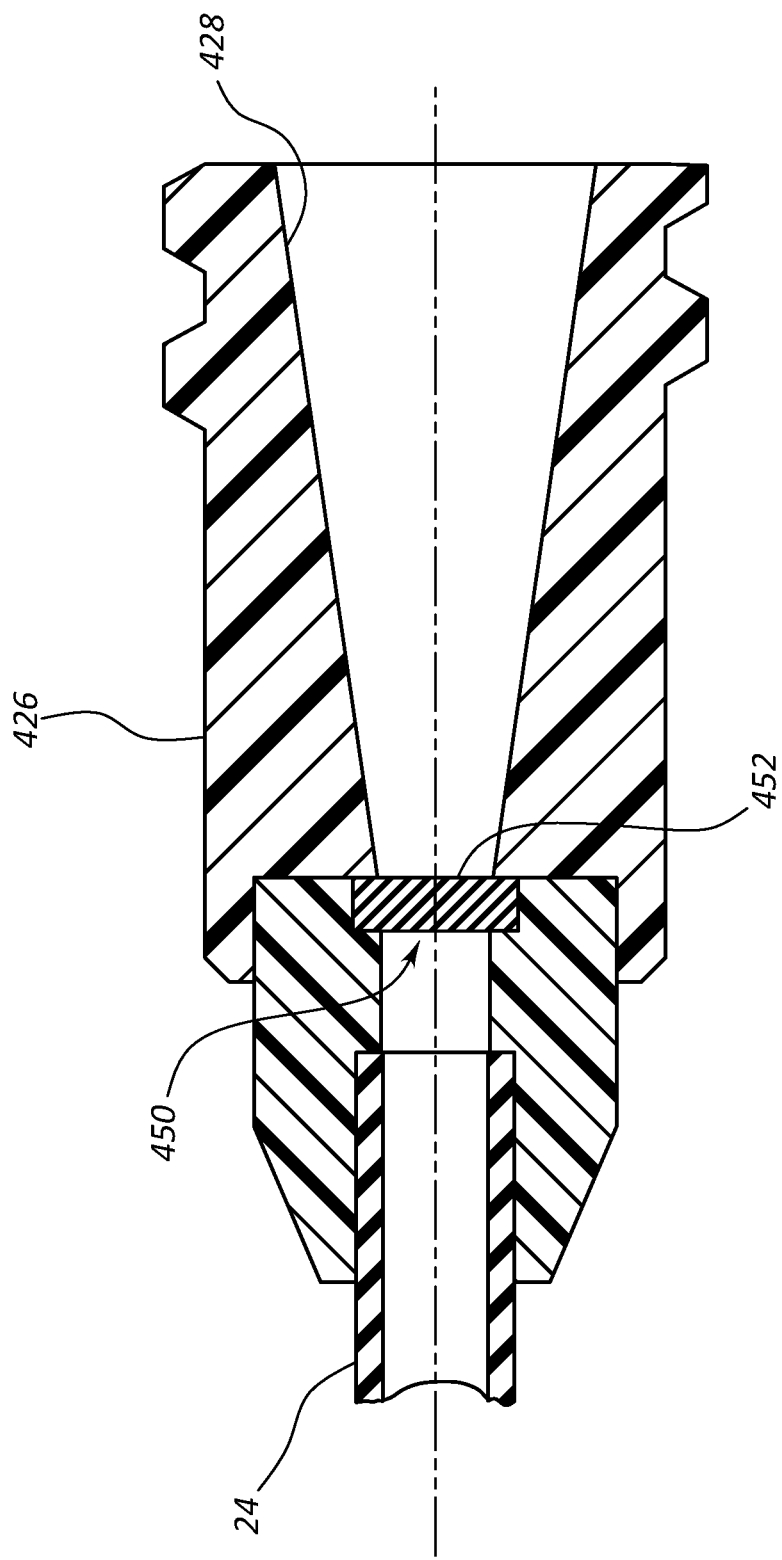

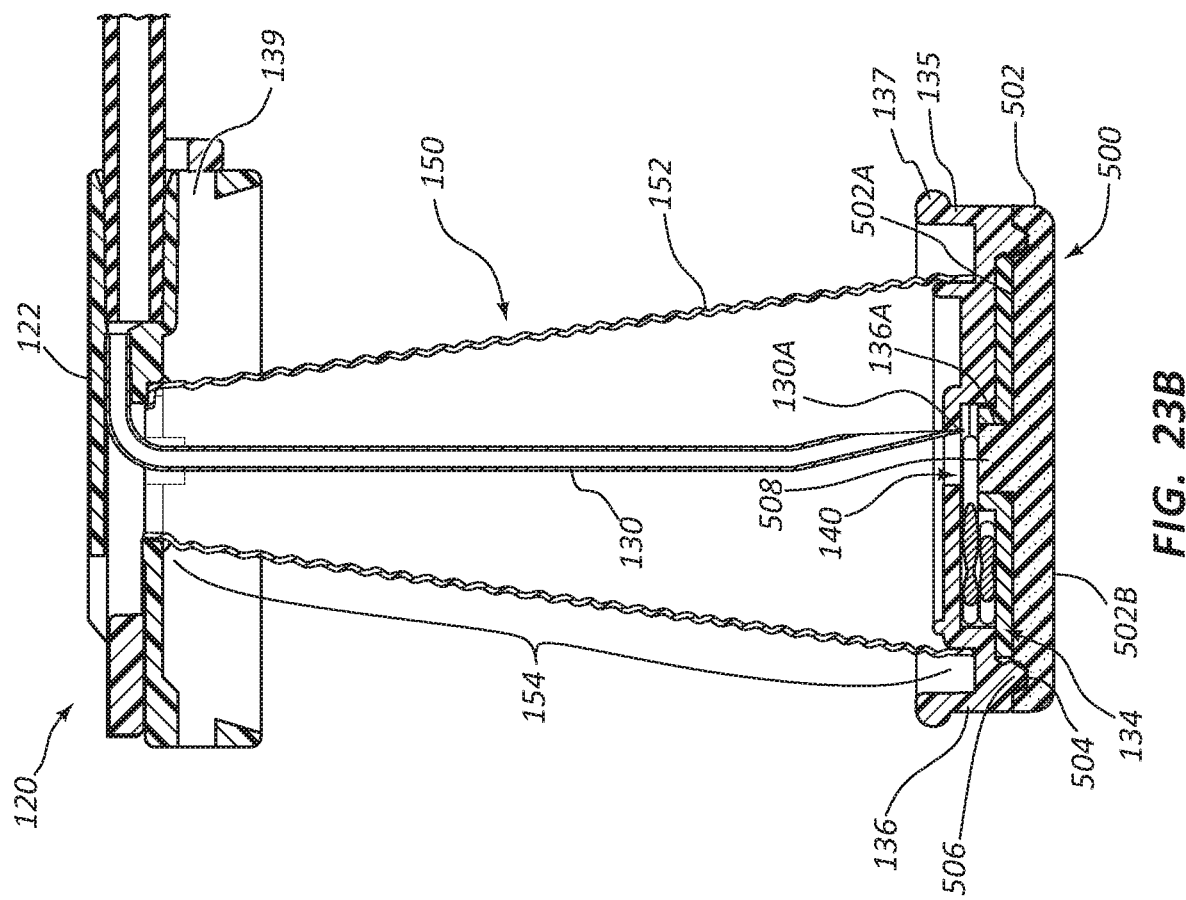
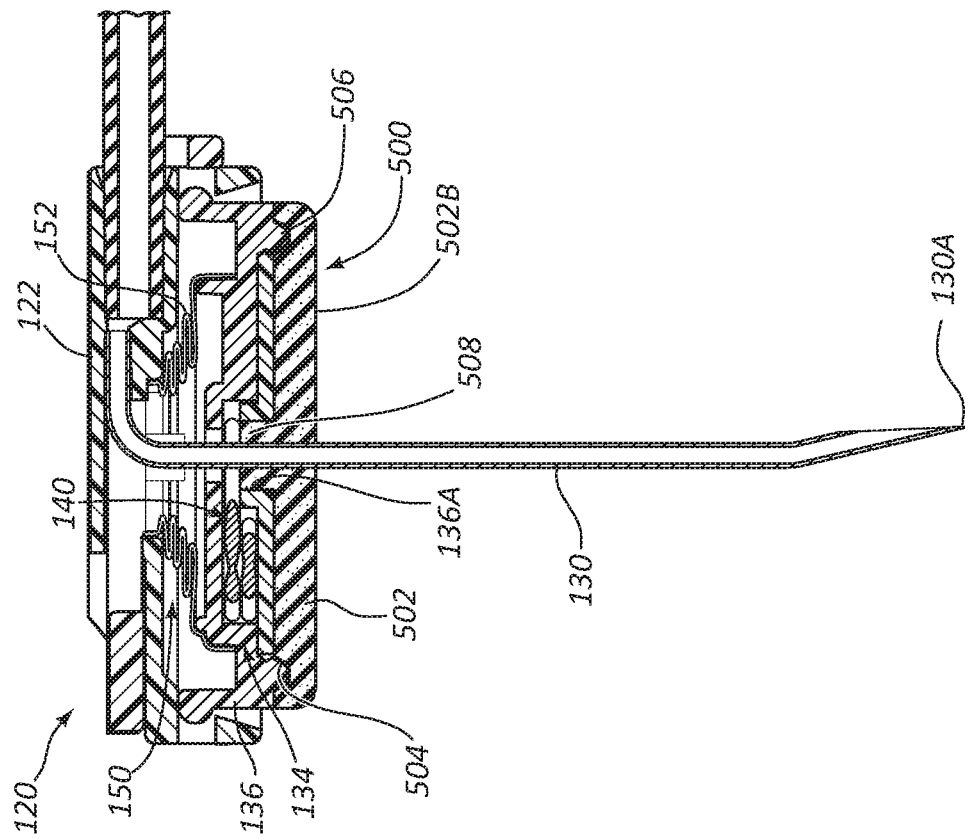

SELF-SEALING PAD FOR A NEEDLE-BASED INFUSION SET

CROSS-REFERENCE TO RELATED APPLICATIONS

This application is a division of U.S. patent application Ser. No. 14/070,246, filed Nov. 1, 2013, which claims the benefit of U.S. Provisional Patent Application No. 61/721,412, filed Nov. 1, 2012, and which is a continuation-in-part of U.S. patent application Ser. No. 13/229,573, filed Sep. 9, 2011, now U.S. Pat. No. 9,248,234, which claims the benefit of U.S. Provisional Patent Application No. 61/381,762, filed Sep. 10, 2010. Each of the foregoing applications is incorporated herein by reference in its entirety.

BRIEF SUMMARY

Briefly summarized, embodiments of the present invention are directed to a safety needle assembly of an infusion set for infusing fluids into a subcutaneously implanted access port. The needle assembly is configured to prevent fluid escape therefrom so as to reduce or prevent fluid exposure to a clinician using the needle assembly.

In one embodiment, the needle assembly comprises a handle portion including a needle extending therefrom, the needle defining a lumen for passage of a fluid therethrough. The needle assembly also includes a safety assembly defining a needle hole through which the needle initially extends. The safety assembly is axially slidable along the needle in order to shield a distal tip of the needle and prevent user contact therewith. A fluid isolation component is included in the safety assembly for isolating fluid escape from the needle to prevent exposure to a clinician.

In one embodiment, a self-sealing pad is included on the safety assembly base through which the needle initially penetrates. When it is later shielded by the safety assembly after use, the needle is also retracted back through the self sealing pad. The pad prevents any fluids that may have leaked from the distal opening of the needle from passing through the pad and escaping the needle assembly, thus preventing unintended exposure to the clinician.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 5 shows a perspective view of the infusion set of FIG. 4 with the safety needle assembly in a second configuration;

FIGS. 7A-7C shows actuation of a safety needle assembly according to another embodiment;

FIGS. 16A and 16B are various views of a safety needle assembly according to one embodiment;

FIG. 17 is a cross sectional side view of a luer connector including a fluid isolation component according to one embodiment;

FIGS. 23A and 23B are various views of the needle assembly of FIGS. 21A and 21B.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a needle placed within the body of a patient is considered a distal end of the needle, while the needle end remaining outside the body is a proximal end of the needle. Also, the words "including," "has," and "having," as used herein, including the claims, shall have the same meaning as the word "comprising."

Embodiments of the present invention are generally directed to a safety infusion set and accompanying needle assembly for infusing fluids, such as chemotherapy agents or other medicaments for example, into an access port or other medical device subcutaneously implanted into the body of a patient. The infusion set and/or needle assembly includes one or more components for isolation of the fluid, including vapors thereof, which may otherwise leak from a needle or other portion of the infusion set. This in turn reduces or prevents possible clinician exposure to the fluid/vapors, which in some cases may be hazardous. Potential harm to the clinician is therefore reduced.

Figure 1:
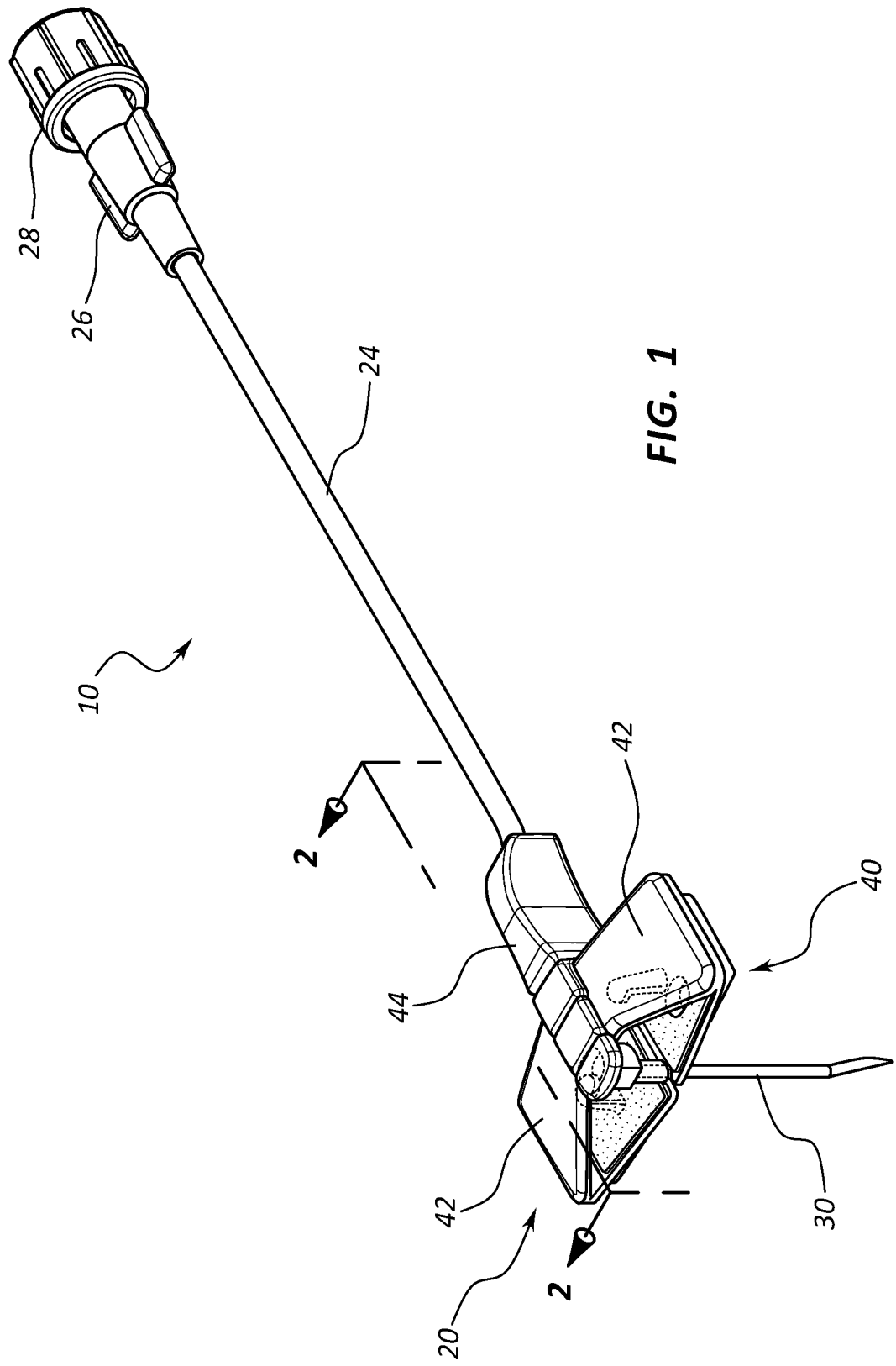
FIG. 1 is a perspective view of an infusion set including a safety needle assembly according to one embodiment.

Reference is first made to FIG. 1, which depicts an infusion set generally designated at 10, including a safety needle assembly ("needle assembly") 20 and one or more extension legs 24. The infusion set 10 is employed to gain access to a subcutaneously implanted access port or other device disposed below the skin of a patient in order to infuse medicaments or other fluids into the patient, and to withdraw fluids therefrom. A luer connector 26 is included on a proximal end of the extension leg 24 so as to enable the infusion set 10 to be placed into fluid communication with a fluid delivery device or system. A cap 28 can be disposed in the luer connector 26 to cover the opening thereof.

FIG. 1 shows that the needle assembly 20 includes a needle 30 extending from a handle 44 and in fluid communication with the tubing of the extension leg 24. A needle safety component 40 is also included in the needle assembly 20, including dual extensible wings that are hinged so as to be selectively extended to substantially cover the length of the needle 30 and isolate a distal end 30A thereof after use of the needle assembly 20 in order to prevent an unintended needle stick of the clinician by the needle tip. Examples of such a hinged safety assembly can be found in U.S. Pat. No. 5,951,522, which is incorporated herein by reference in its entirety.

Figure 2:
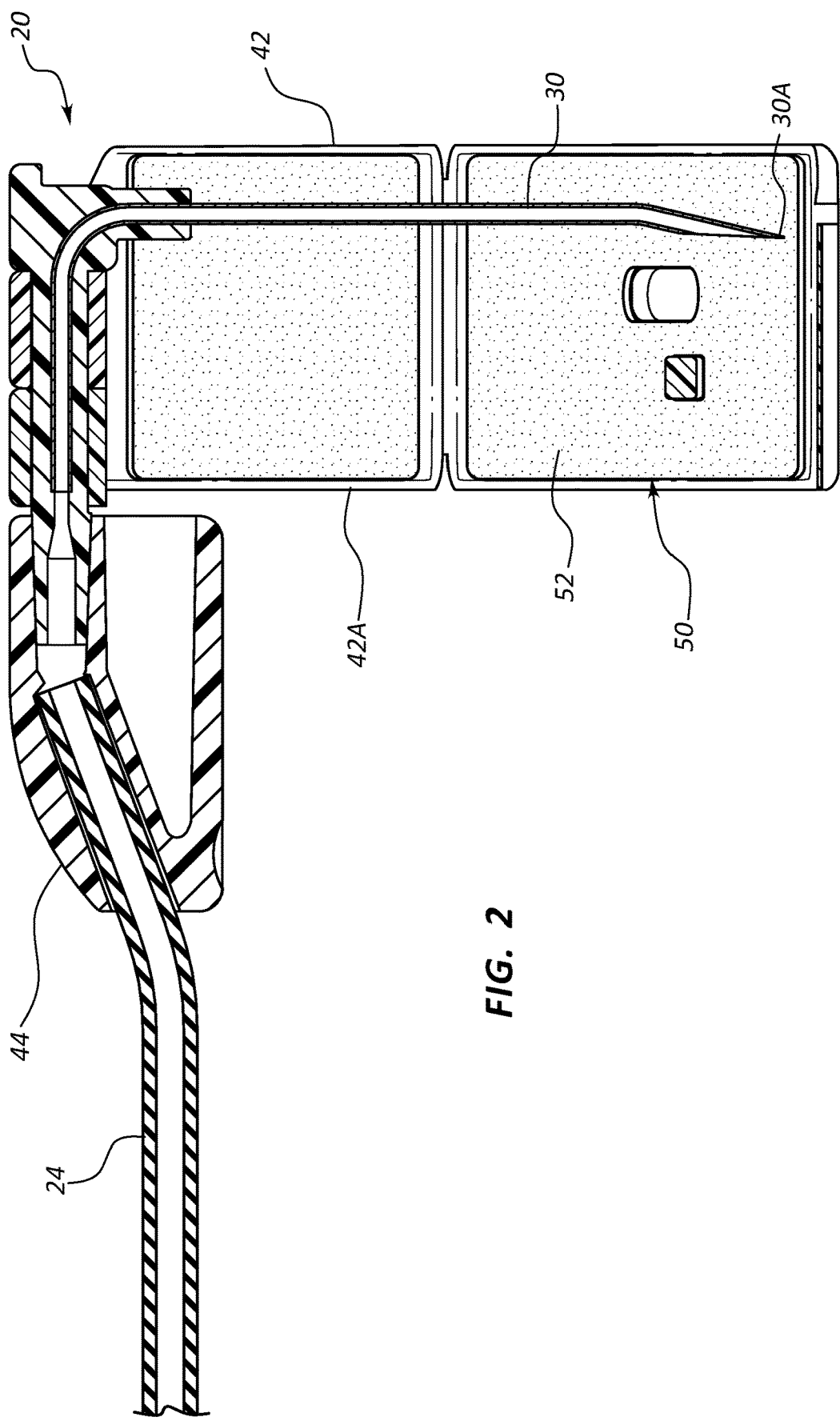
FIG. 2 is a side view of the needle assembly of FIG. 1.

As best seen in FIG. 2, the needle assembly 20 further includes a fluid isolation component 50 for isolating any fluid or vapor that may unintentionally escape from the needle 30 during use of the needle assembly. Specifically, the fluid isolation component 50 in the present embodiment includes absorbent pads 52 disposed on an inner surface 42A of each wing 42 of the needle safety component 40. The pads 52 are disposed such that when the wings 42 of the needle safety component 40 are deployed to cover the distal tip 30A of the needle 30 (FIG. 2), the pads sandwich the body and distal tip of the needle therebetween. Any fluid present on an external surface of the needle or any fluid/vapor leaking from the distal end thereof is captured and absorbed by the pads 52, thus preventing escape of the fluid, which as mentioned above may contain hazardous substances. This in turn protects the clinician from fluid exposure.

Figure 3C:
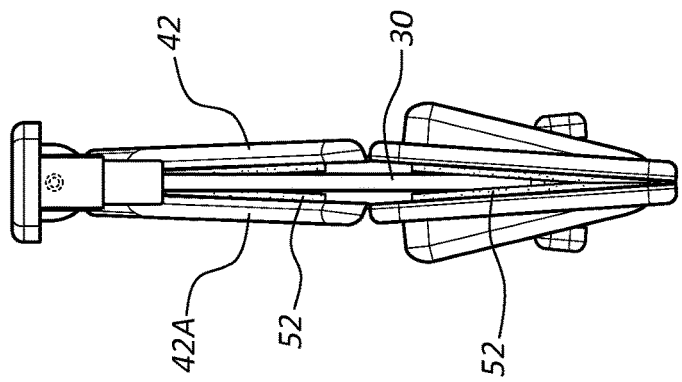
FIGS. 3A-3C show actuation of needle assembly of FIG. 1.
Figure 3B:
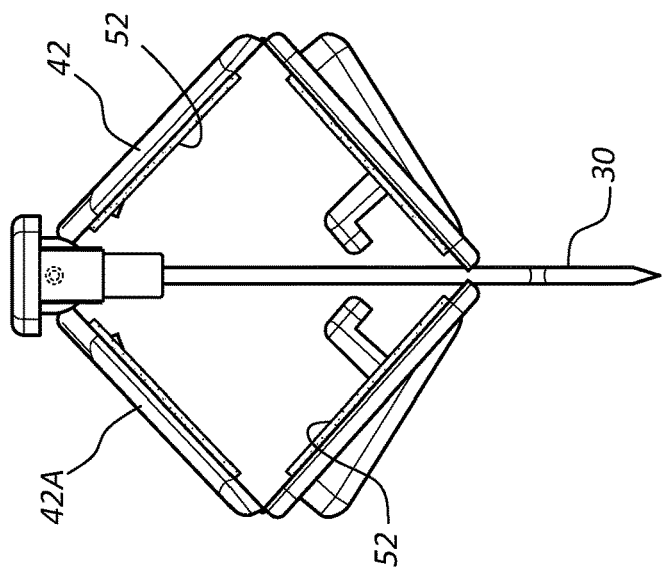
Figure 3A:
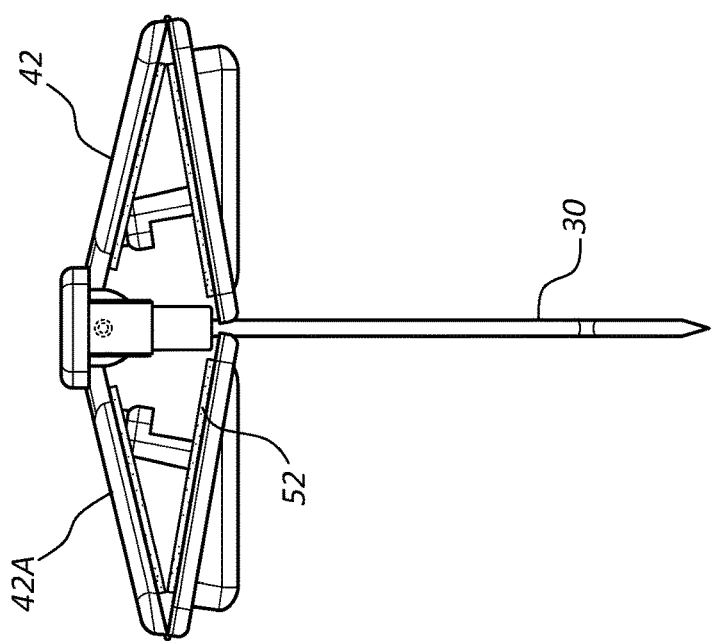

FIGS. 3A-3C show the manner in which the wings 42 of the needle safety component 40 extend to cover the needle 30 and its distal tip 30A, and additionally the manner in which the pads 52 sandwich and partially encapsulate the needle 30, including its external surfaces and its distal tip 30A, to prevent fluid/vapor escape. In one embodiment, the pads 52 can include an absorbent foam and/or rubber material, though many other suitable materials can be employed, including activated charcoal, etc.

Figure 4:
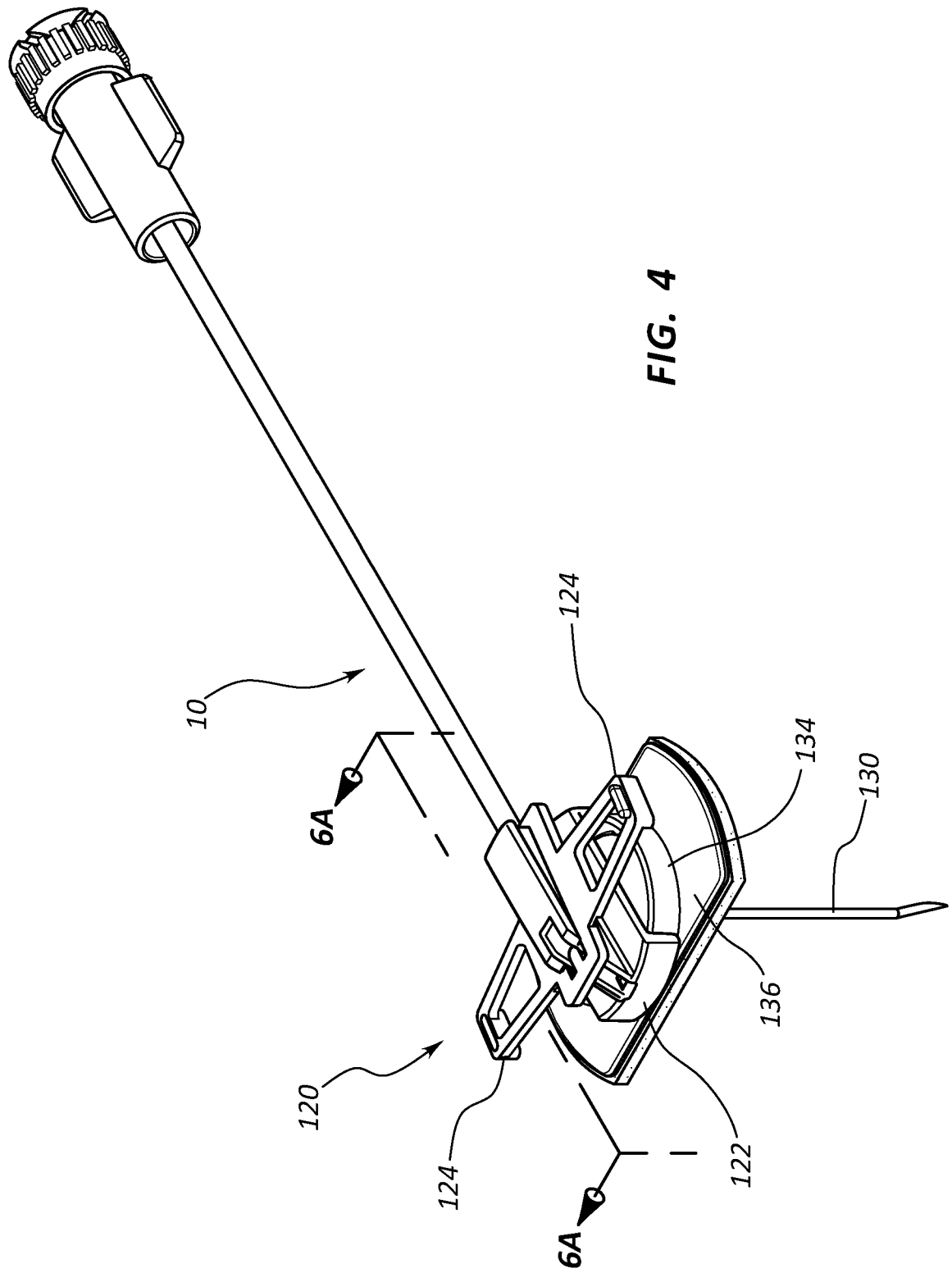
FIG. 4 shows a perspective view of an infusion set including a safety needle assembly in a first configuration according to one embodiment.

FIGS. 4 and 5 show the infusion set 10 including a needle assembly 120 according to another embodiment, wherein the needle assembly includes a handle portion 122 with handles 124 extending therefrom. A needle 130 extends from the handle portion 122 and initially through a safety assembly 134 that is slidably disposed with respect to the needle 130 so as to be axially slidable therewith. The safety assembly 134 includes a base 136 that houses a needle safety component 140 (FIGS. 8A, 8B) for shielding a distal tip 130A of the needle 130 when use of the needle assembly is complete.

Figure 6C:
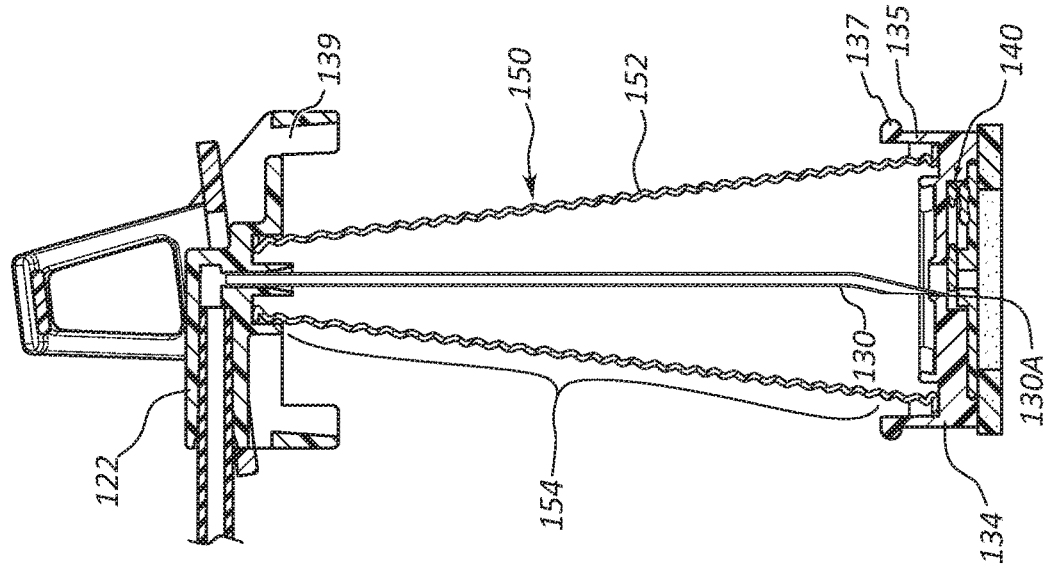
FIGS. 6A-6C show actuation of the safety needle assembly of FIGS. 4 and 5
Figure 6B:
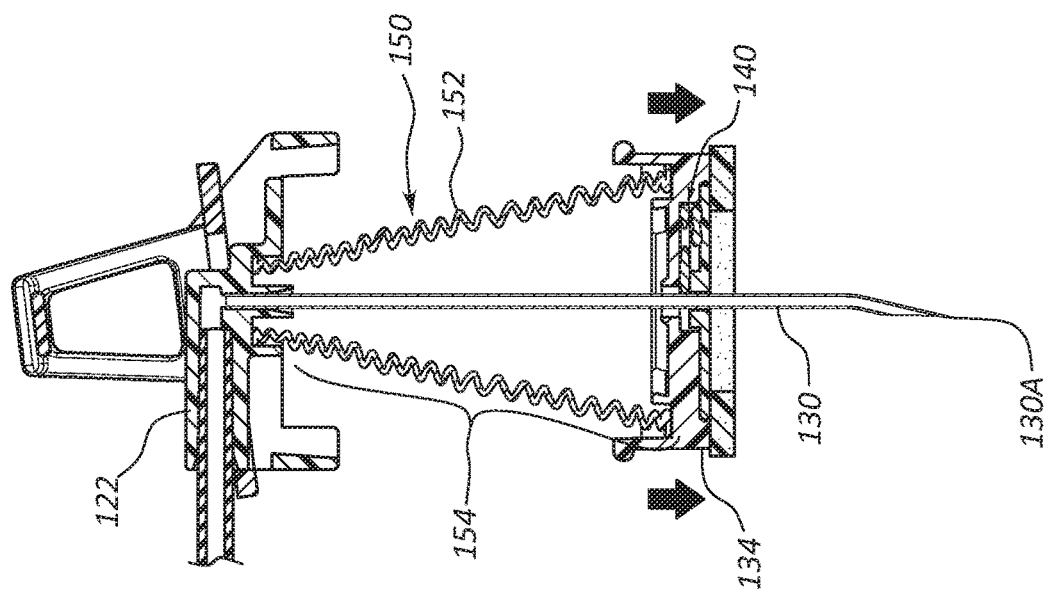
Figure 6A:
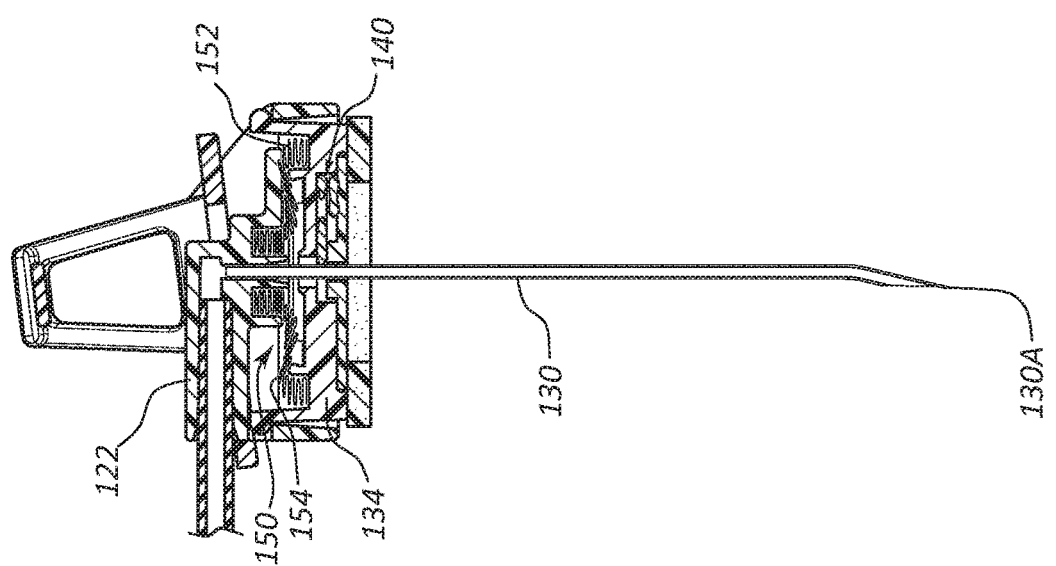

The needle assembly 120 further includes a fluid isolation component 150 for isolating any fluid or vapor that may unintentionally escape from the needle 130 during use of the needle assembly. Specifically, the fluid isolation component 150 in the present embodiment includes a conically shaped, extensible shroud 152 disposed about the body of the needle 130 and extending between the handle portion 122 and the axially slidable safety assembly 134. Including plastic such as PET or other substantially impermeable, collapsible, and suitable durable material, the shroud 152 forms a hollow cone about the needle 130 and is corrugated with corrugations 154 in a bellows-like manner to enable it to fold up compactly when the safety assembly 134 is undeployed (FIG. 4) and to extend to cover and substantially encompass the needle 30 when the safety assembly 134 is deployed (FIG. 5), i.e., the safety assembly is axially slid down the needle 130 toward the distal tip 130A such that the needle safety component 140 shields the distal tip. FIGS. 6A-6C depict the manner of deployment of the safety assembly 134 and the extension of the corrugated shroud 152. In the extended state shown in FIGS. 5 and 6C, the shroud 152 assists in isolating fluids/vapors present on the needle 130 or emitted from the needle distal tip 130A from contact with the clinician.

Note that examples of safety needles that can utilize principles discussed here and in other embodiments herein can be found in the following United States patents: U.S. Pat. No. 7,717,888; U.S. Pat. No. 8,066,678; U.S. Pat. No. 8,597,253; and U.S. Pat. No. 8,231,582. Each of the aforementioned patents/patent applications is incorporated herein by reference in its entirety.

The shroud 152 as the fluid isolation component 150 can include other configurations. One such configuration is shown in FIGS. 7A-7C, wherein the shroud includes a plurality of interlocked, telescoping segments that are extendible to cover and encompass the needle body when the safety assembly 134 is deployed (FIG. 7C). When the safety assembly 134 is undeployed, the telescoping segments 156 are stacked together, as shown in FIG. 7A. Again, these and other configurations for encompassing the needle body illustrate manners by which a fluid isolation component can isolate the needle body and tip in order to prevent fluid exposure to clinician. As best seen in FIG. 7C, the axially slidable safety assembly 134 includes at least one proximally-extending protrusion 135. The proximally-extending protrusion 135 may also include a lip 137 at a proximal end of the proximally-extending protrusion 135. As best seen in FIG. 7A, the proximally-extending protrusion 135 and associated lip 137 may be configured to co-operate with groove 139 in handle portion 122 to maintain the assembly in a retracted position.

Figure 8A:
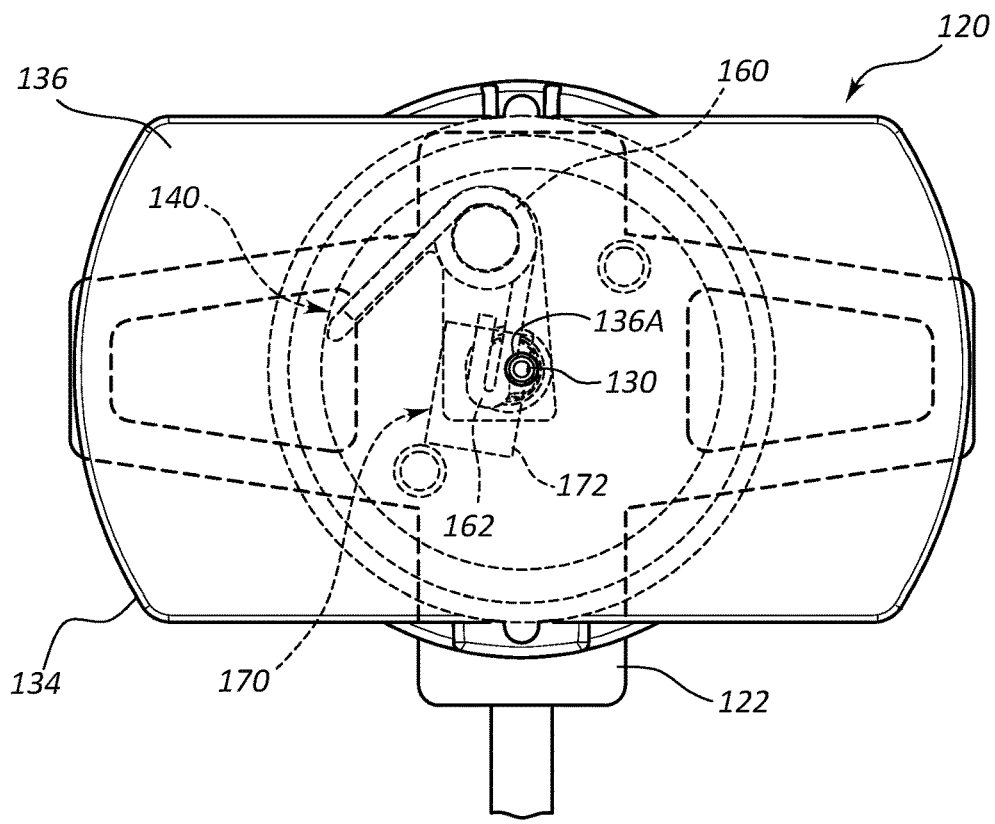
FIGS. 8A and 8B show a bottom view of a safety needle assembly including a fluid isolation component according to one embodiment.
Figure 8B:
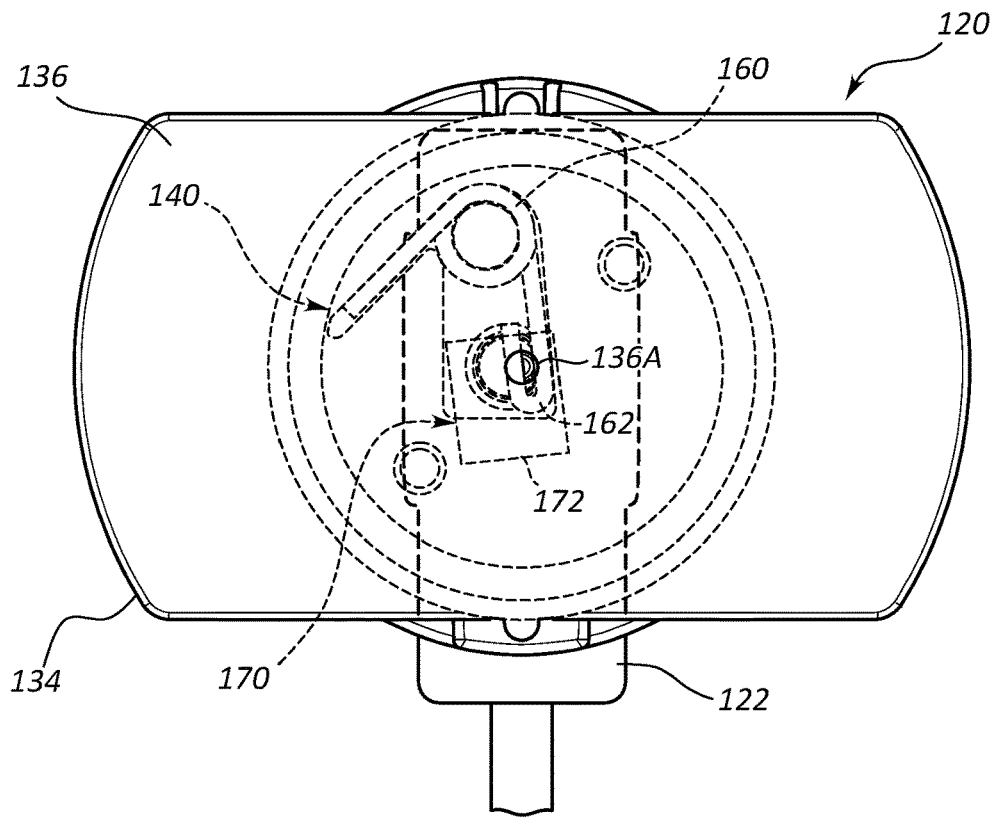

FIGS. 8A and 8B depict details of the needle safety component 140 of the needle assembly 120 of FIGS. 4-7C. Particularly, FIGS. 8A and 8B depict bottom views of the needle assembly 120. The needle safety component 140 is shown, including a coiled wire torsion spring 160 included within the base 136 of the safety assembly 134. The spring includes at one end thereof an obstruction component, i.e., a looped portion 162 that is biased to lie against the needle 130 when the needle extends through a hole 136A defined in the base 136 of the safety assembly 134, as shown in FIG. 8A. As shown in FIG. 8B, once the distal tip of the needle 130 is withdrawn into the base 136 in connection with extension of the safety assembly 134 (e.g., FIGS. 5, 6C, 7C), the spring 160 expands such that the looped portion 162 slides over the needle hole 136A to prevent re-emergence of the needle distal tip.

In addition, a fluid isolation component 170 is included with the spring 160 for isolating any fluid or vapor that may unintentionally escape from the needle 130 during use of the needle assembly. Specifically, the fluid isolation component 170 includes a shield 172, shown in FIGS. 8A and 8B, which is attached proximate the looped portion 162 of the spring 160. Thus, when the looped portion 162 slides over to prevent re-emergence of the distal tip 130A of the needle 130 through the hole 136A (FIG. 8B), the shield fully covers and occludes the hole so as to prevent any fluid/vapor leaking from the distal tip of the needle from exiting through the hole and potentially contaminating the environment or clinician. The shield 172 thus serves to occlude the hole 136A and isolate any fluids/vapors from the clinician. Note that the particular size, shape, and configuration of the shield can vary from what is shown and described herein, as can the particular configuration of the needle assembly. In one embodiment, it is appreciated that the shield can include an absorbent material so as to absorb any leaked fluid.

Figures 9A, 9B:
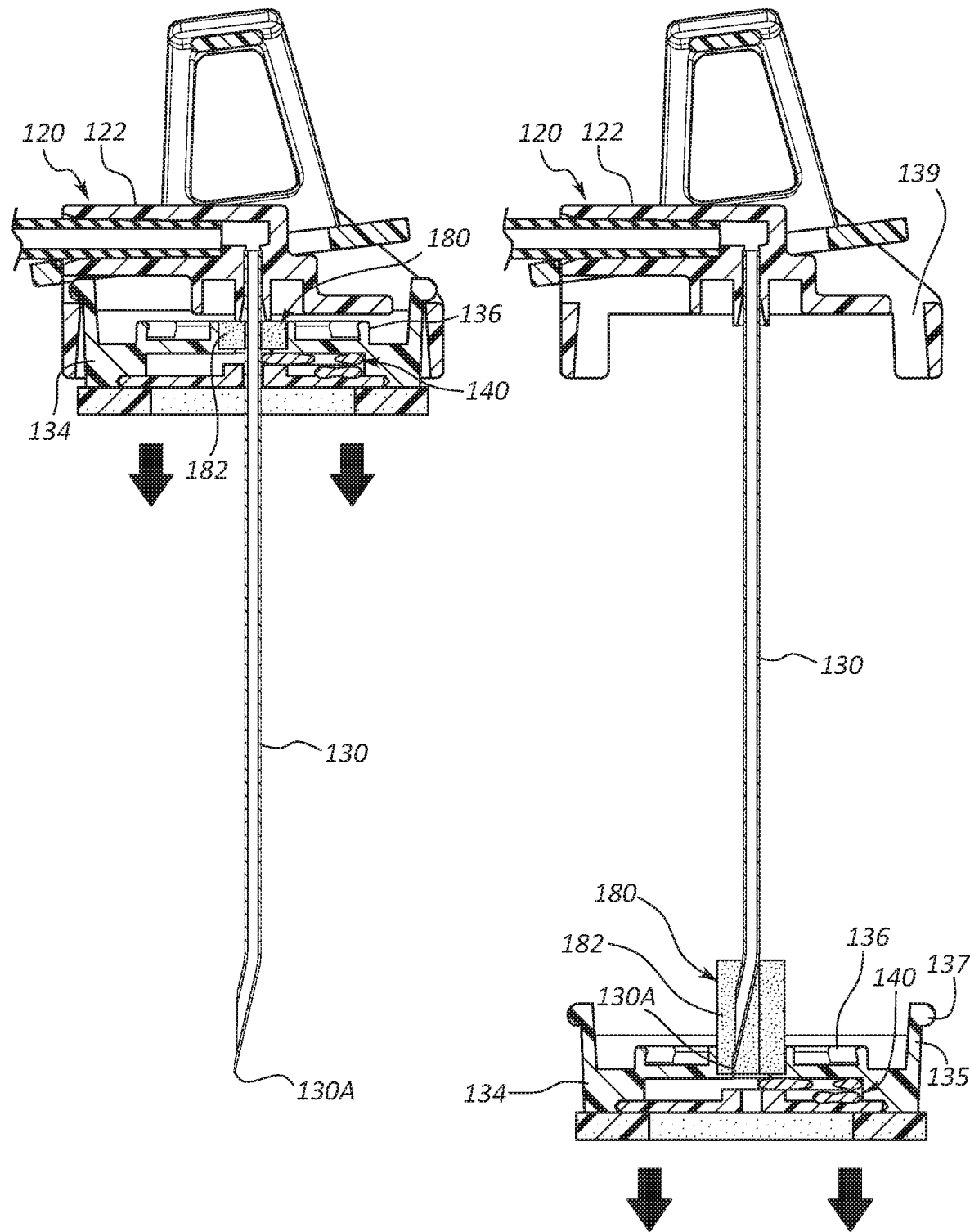
FIGS. 9A and 9B are cross sectional side views of a safety needle assembly including a fluid isolation component according to one embodiment.

FIGS. 9A and 9B depict details of the needle assembly 120 according to another embodiment, including a fluid isolation component 180 for isolating any fluid or vapor that may unintentionally escape from the needle 130 during use of the needle assembly. As shown, the fluid isolation component 180 in the present embodiment includes a cylindrical absorption plug 182 included with the axially slidable safety assembly 134 of the needle assembly 120 and including a central cavity so as to be positioned about a portion of the body of the needle 130 (FIG. 9A). The central cavity of the plug 182 is sized such that the plug is able to wipe the outer surface of the body of the needle 130 as the safety assembly 134 is axially slid down the needle toward the distal tip 130A thereof, thus removing fluid from the outer needle surface and capturing it in the plug itself. In addition, once the safety assembly 134 has fully shielded the needle distal tip 130A (FIG. 9B), the plug 182 is positioned about the distal opening of the lumen of the needle 130 so as to catch and absorb any fluids/vapors emanating therefrom.

It is appreciated that the absorption plug can include a variety of size, type, and material configurations, and can be employed on a variety of needle-based devices where residual fluid/vapor capture is desired. In one embodiment, for instance, the absorption member includes activated charcoal. In other embodiments, other materials and membranes can be employed, including silica gel, clays, activated alumina, zeolites, 0.2 micron or other filtration material, etc. The description included herein is therefore not intended to limit the present disclosure in any way.

Figure 10:
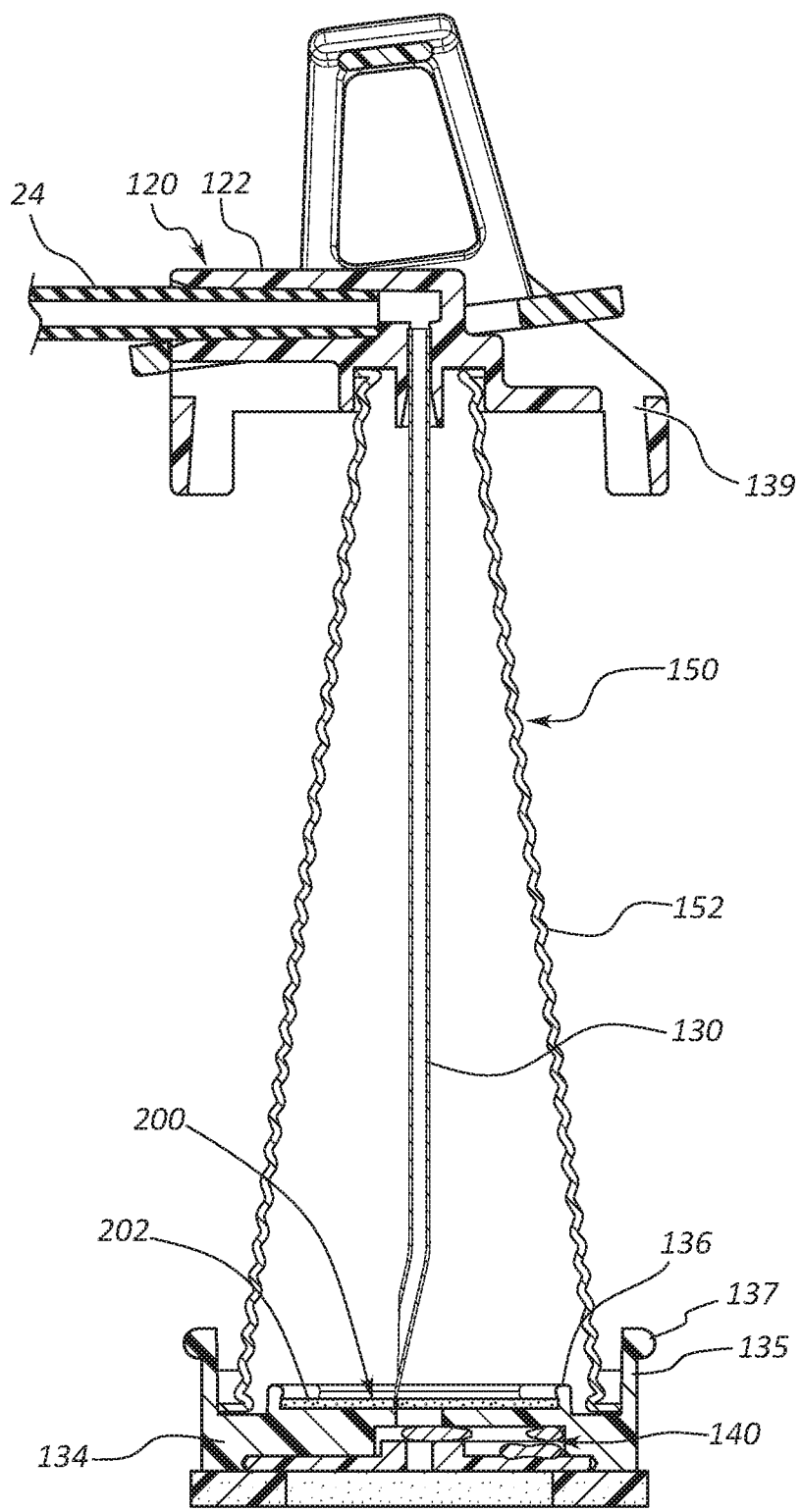
FIG. 10 is a cross sectional side view of a safety needle assembly including a fluid isolation component according to one embodiment.

FIG. 10 shows details of a fluid isolation component 200 according to another embodiment, including an absorption disk 202 included with the safety assembly 134. The absorption disk 202 is disposed above the needle safety component 140 in the safety assembly base 136 and is slit to enable the needle 130 to pass therethrough. Extension of the safety assembly 134 down the length of the needle 130 enables the absorption disk 202 to wipe the outer needle surface so as to remove any fluid present thereon. In addition, once the safety assembly 134 is fully extended to shield the needle 130 (FIG. 10), the absorption disk 202 is positioned so as to absorb any fluid/vapor leaking from the distal lumen opening at the needle distal tip 130A. As with the previous embodiment, the absorption disk 202 in one embodiment includes activated charcoal or other suitable, absorbent material as outlined above in connection with the absorption plug 182 shown in FIGS. 9A and 9B. The position, shape, thickness or other configuration of the absorption disk can vary from what is shown and described herein.

Figure 11:
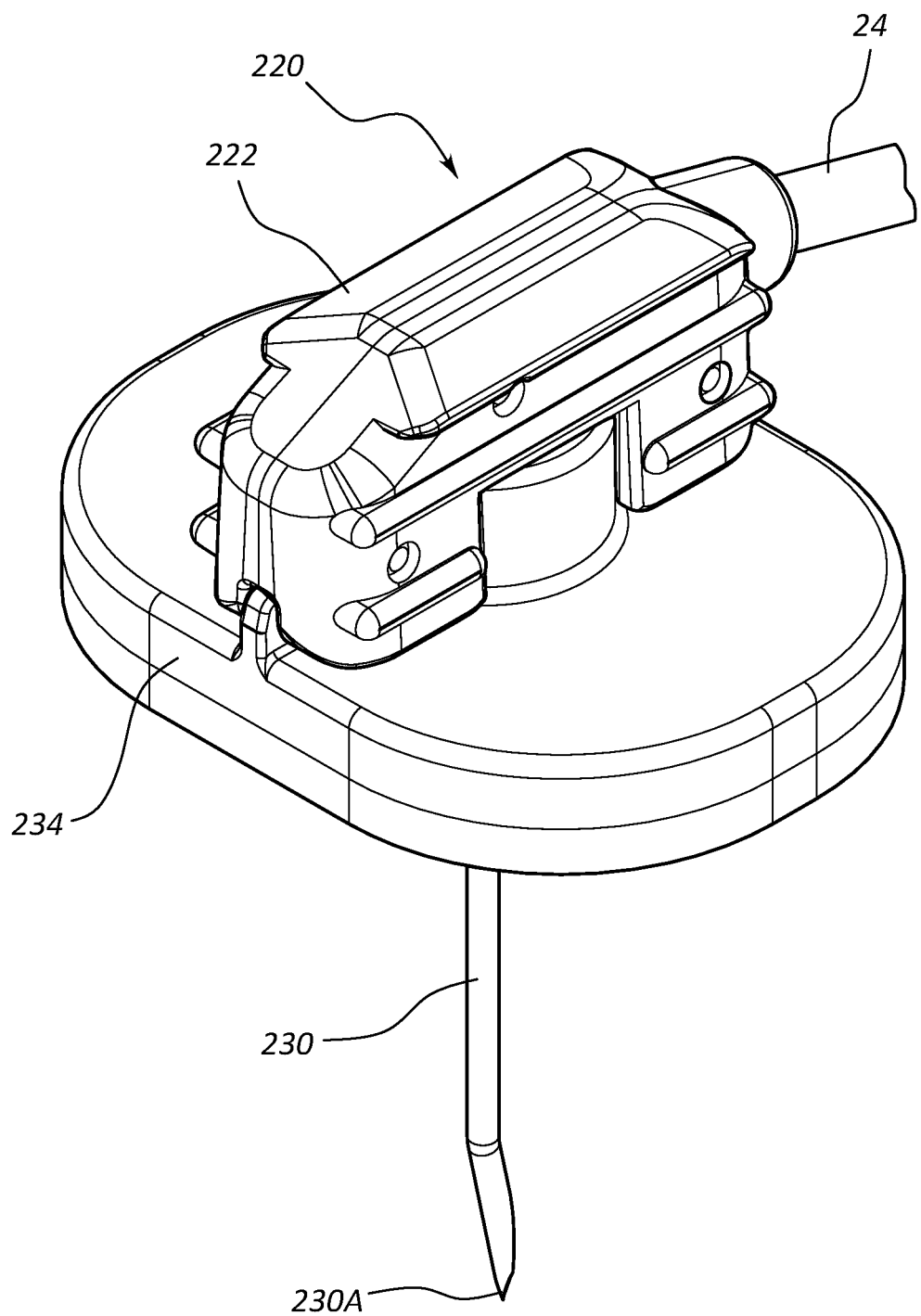
FIG. 11 is a perspective view of a safety needle assembly according to one embodiment.
Figure 12A:
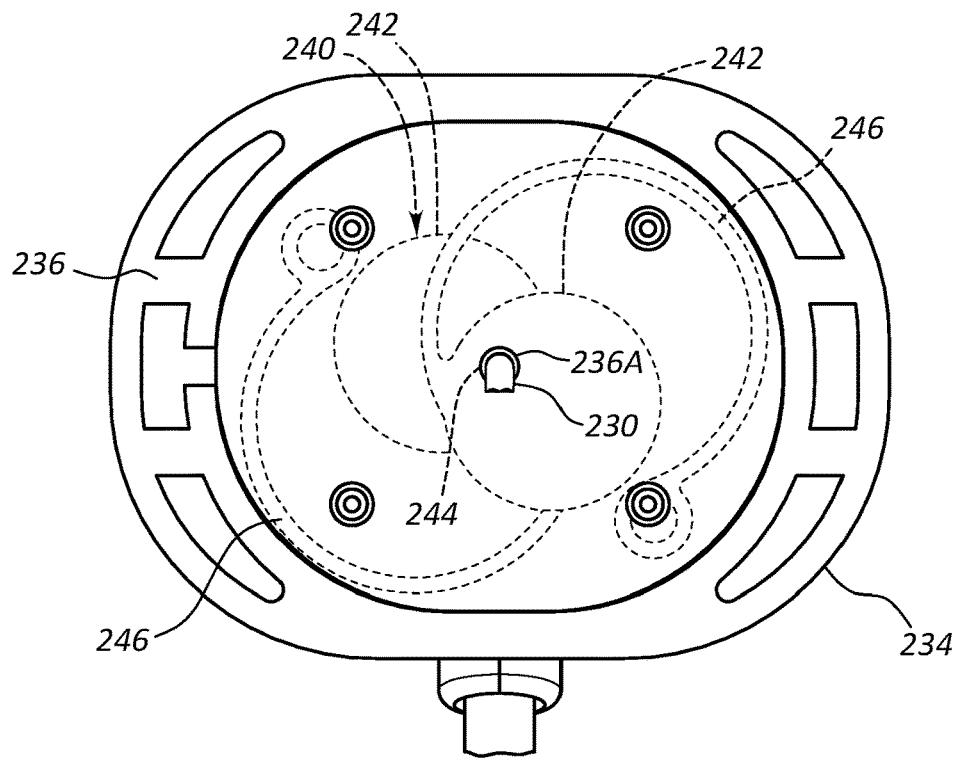
FIGS. 12A and 12B are bottom views of the safety needle assembly of FIG. 11.
Figure 12B:
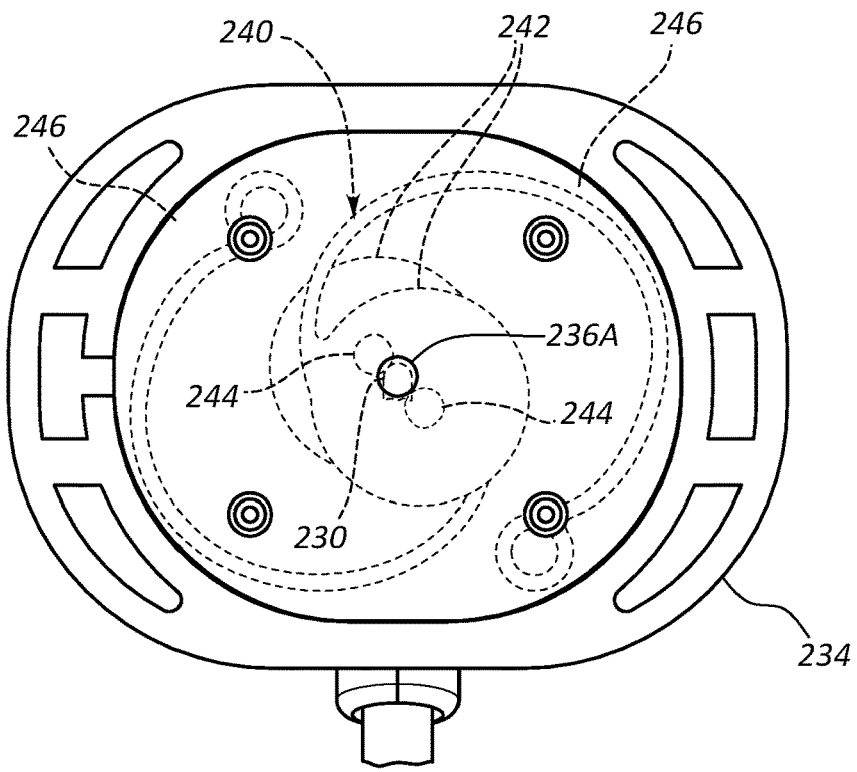

FIGS. 11-12B depict various details of a needle assembly 220 that can include a fluid isolation component, according to one embodiment. As shown, the needle assembly 220 includes a handle portion 222 from which extends a needle 230. The needle 230 initially extends through a safety assembly 234 that is slidably disposed with respect to the needle so as to be axially slidable therewith. The safety assembly 234 includes a base 236 that houses a needle safety component 240 (FIGS. 12A, 12B) for shielding a distal tip 230A of the needle 230 when use of the needle assembly is complete.

In greater detail, FIGS. 12A and 12B show that the needle safety component 234 includes two spring-based shutters 242 that each define a hole 244 through which the needle 230 passes when the needle extends through the safety assembly 234 and out a hole 236A defined in the base 236, such as in the configuration shown in FIG. 11. The shutters 242 each further include a spring arm 246. As seen in FIG. 12A, when the safety assembly 234 is undeployed (FIG. 11), the holes 244 of the shutters 242 are aligned so that the needle 230 passes therethrough. This constrains the shutters 242 and spring arms 246 into the configuration shown in FIG. 12A.

When the safety assembly 234 is actuated, however, it is slid down the length of the needle 230 so as to cause the needle distal tip 230A to recede from the hole 236A and the shutter holes 244 so as to be shielded within the safety assembly base 236. As shown in FIG. 12B, this causes the shutters 242 to no longer be constrained by the needle 230 and enables the shutter spring arms 246 to slide the shutters laterally within the base 236 so as to cover and occlude the hole 236A defined in the base, thus preventing reemergence of the needle distal tip 230A. Note that further information regarding this and other related needle safety assemblies can be found in U.S. Pat. No. 6,585,704 to Luther et al., entitled "Method of Retaining a Tip Protector on a Needle with a Curved Tip."

Figure 13:
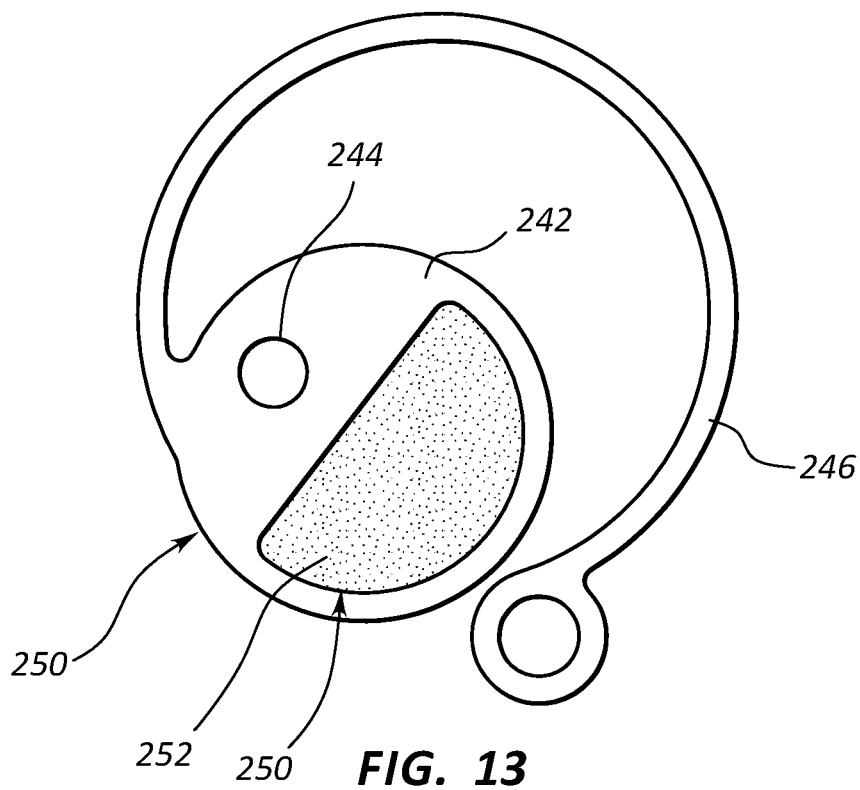
FIG. 13 is a top view of a shutter of the safety needle assembly of FIG. 10, including a fluid isolation component according to one embodiment.
Figure 14:
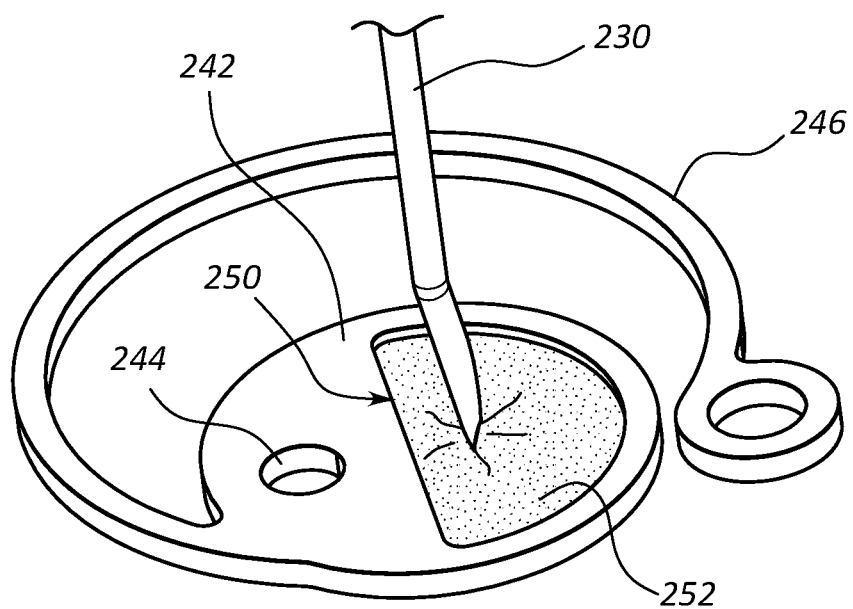
FIG. 14 is a perspective view of the shutter of FIG. 13 including the fluid isolation component.

In accordance with one embodiment the needle assembly 220 includes a fluid isolation component 250 for isolating any fluid or vapor that may unintentionally escape from the needle 130 during use of the needle assembly. Specifically, the fluid isolation component 250 in the present embodiment includes an absorption pad 252 disposed on a backside of one or both of the shutters 242 of the safety assembly 234. As shown in FIGS. 13 and 14, the pad 252 is disposed on the shutter 242 so that the distal tip 230A of the needle 230 rests against it after the distal tip has been withdrawn and shielded by the base 236 of the safety assembly 234. Should any fluid leak from the distal opening of the lumen of the needle 230, it can be readily captured by the pad 252, thus preventing its escape outside of the safety assembly 234. The pad can include one or more of suitable materials including those listed above in connection with the embodiment of FIGS. 9A and 9B, silicone, rubber, etc. As shown, the pad can also be recessed within the shutter 242 so as to provide a basin for capture of the fluid, in one embodiment. Note that the pad and shutters can vary in size, number, shape, design, etc.

Figure 15:
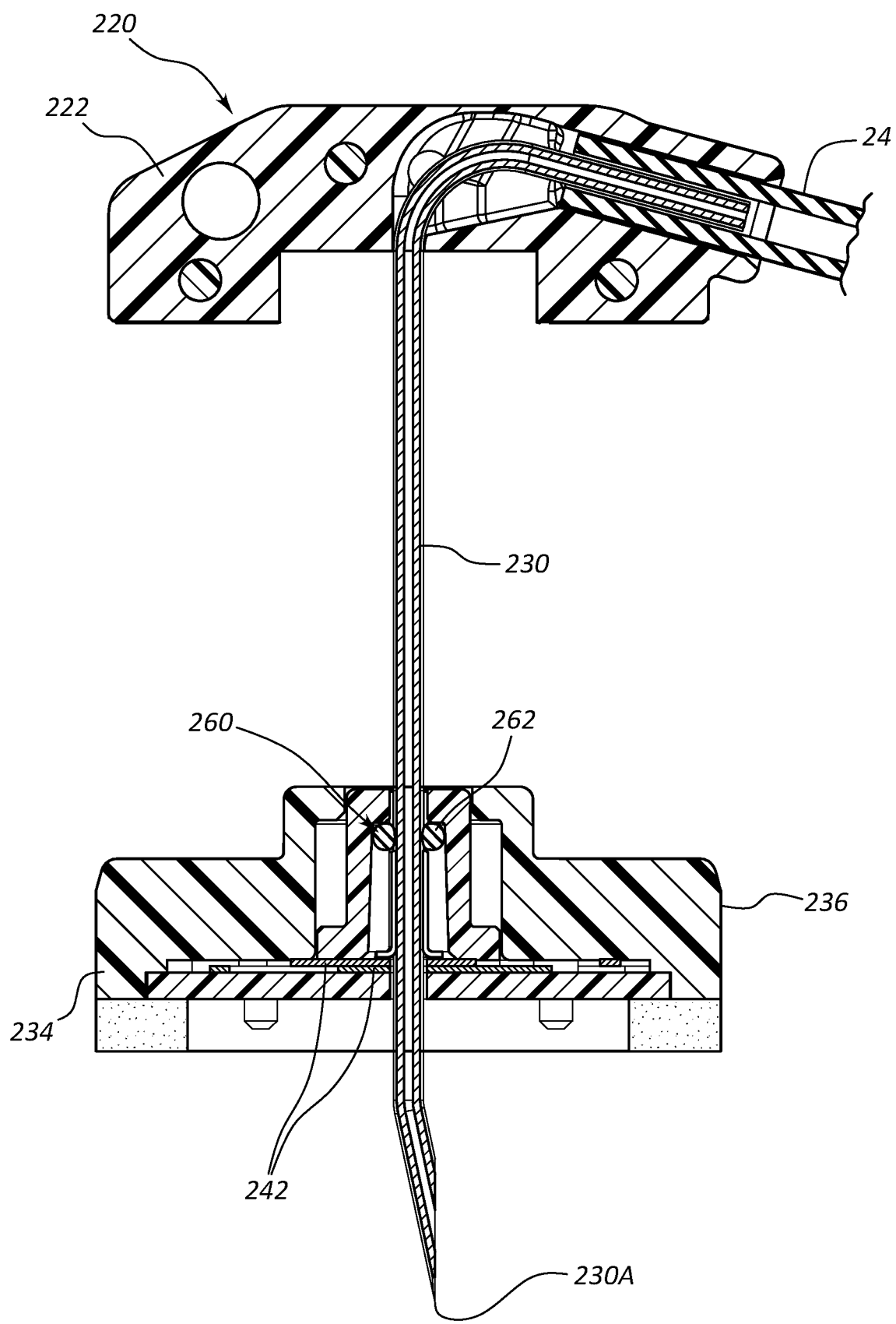
FIG. 15 is a cross sectional side view of a safety needle assembly according to one embodiment.

FIG. 15 shows the needle assembly 220 including a fluid isolation component 260 according to one embodiment, wherein the fluid isolation component includes an O-ring 262 that is disposed within the safety assembly 234 about a portion of the needle 230. So positioned, the O-ring 262 wipes the length of the needle 230 when the safety assembly 234 is axially slid down the needle in order to shield the needle distal tip 230A. The O-ring 262 is sized such that its wiping action cleans the outer needle surface of any fluids that might otherwise be exposed to the clinician and prevents their escape from the safety assembly base 236. In one embodiment, the O-ring can be configured to be absorbent so as to soak up any fluid it comes into contact with during wiping of the needle. Note that the O-ring can be placed in other locations with respect to the needle safety assembly and that the needle housing and safety assembly can vary in configuration from what is shown.

FIGS. 16A and 16B depict various details of a needle assembly 320 including a fluid isolation component, according to one embodiment. The needle assembly 320 includes a handle portion 322 from which extends a needle 330. The needle 330 initially extends through a hole 344 defined in a safety assembly 334 that is pivotally movable with respect to the handle portion 322 and the needle 330 via a hinge point 338. The safety assembly 334 houses a needle safety component 340 including a laterally slidable shutter 342, disposed in a shutter cavity 346, for shielding a distal tip 330A of the needle 230 when use of the needle assembly is complete. A foam pad 354 is disposed on the bottom of the safety assembly 334.

As shown in FIG. 16B, the needle 330 is biased while residing in the hole 344 of the safety assembly 334 such that when the distal tip 330A is withdrawn from the hole, the needle 330 urges the shutter 342 to laterally slide within the shutter cavity 346, thus covering the hole and preventing re-emergence of the needle distal tip. In another embodiment, the shutter itself can be biased to urge the needle distal tip laterally.

The needle assembly 320 further includes a fluid isolation component, here configured as an extensible shroud 352 that extends about the needle 330 between the handle portion 322 and the safety assembly 334 to isolate the body of the needle and any vapors present therewith. Thus, the shroud 352 provides isolation of fluids present on the needle 330. In addition, the shutter 342 provides some fluid isolation as well.

Figure 18B:
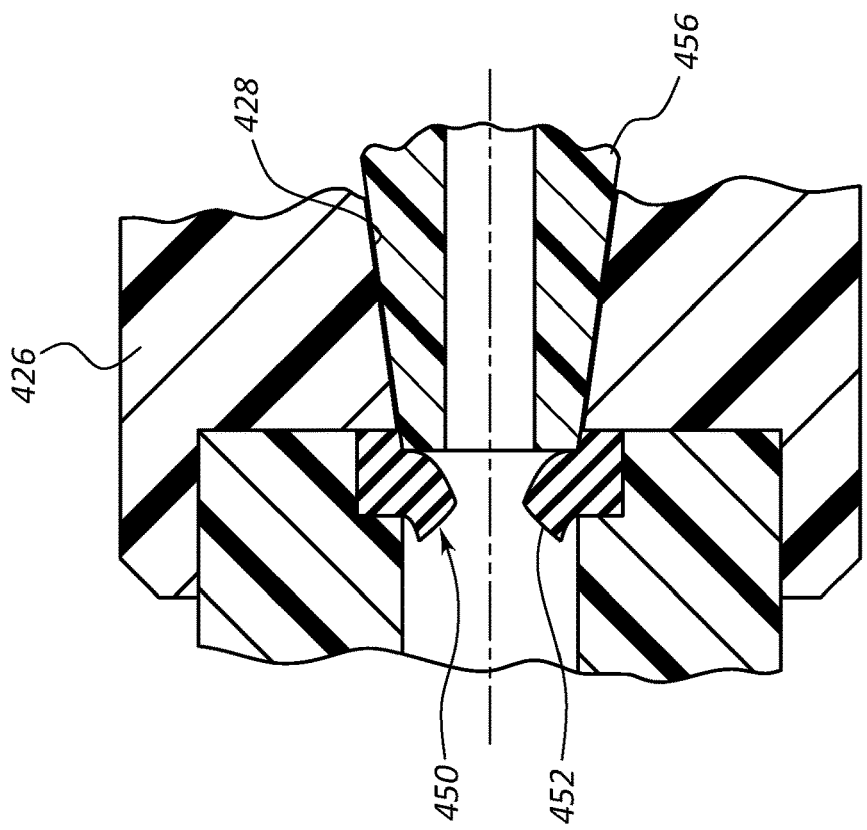
FIGS. 18A-18B are cross sectional side views of the luer connector of FIG. 17 during use.
Figure 18A:
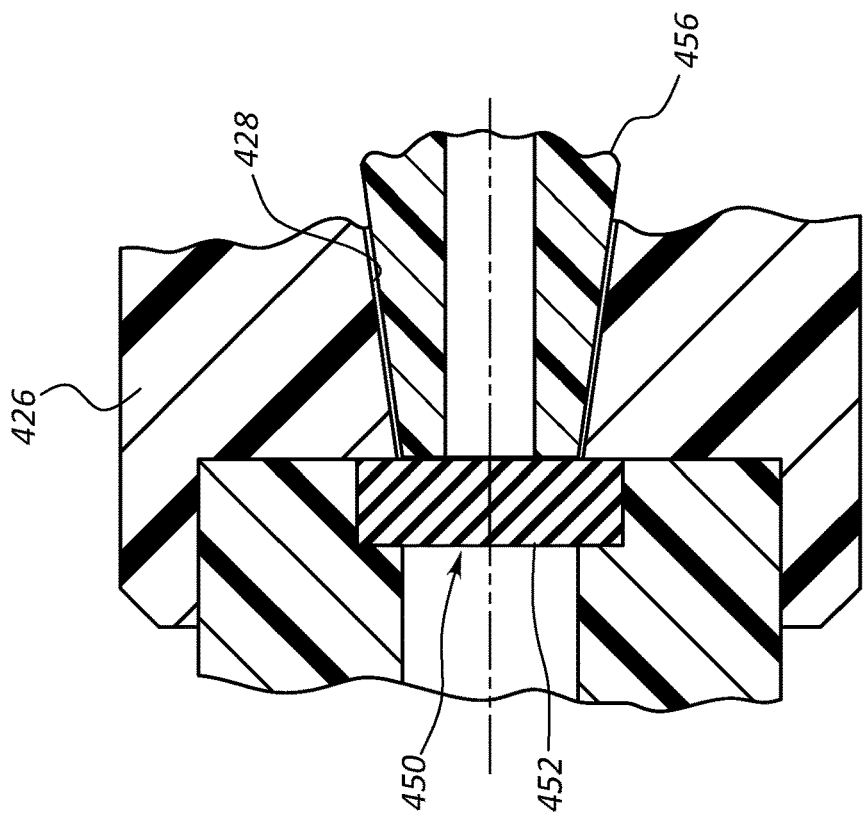

FIGS. 17-18B disclose a luer connector 426 including a fluid isolation component, according to one embodiment. As shown, the connector 426 is a female-type luer connector, though the principles described here can be extended to other connective or fluid-carrying components of an infusion set or other suitable fluid delivery medical device. Connected to the extension leg tubing 24, the connector 426 includes a body that defines a cavity 428 suitable for receiving a male-type connector 456 (FIGS. 18A, 18B) therein. The connector 426 can include threads to enable the male connector 456 to threadably connect therewith. The cavity 428 defines a portion of a fluid pathway through the connector body.

A fluid isolation component 450 is included in the connector 426. In particular, the fluid isolation component 450 in the present embodiment includes a slit valve 452 that is disposed in the fluid pathway defined by the connector 426. Other suitable types of valves may also be employed.

As seen in FIGS. 18A and 18B, when the male connector 456 is received but not fully seated within the cavity 428 of the female connector 426, the valve 452 remains closed, thus isolating any fluid contained in the extension leg tubing 24 attached thereto. When the male connector 456 is fully inserted into the female connector 426, the distal end of the male connector engages and opens the valve 452, thus allowing fluid flow therethrough. This configuration of the connector 426 thus serves as one example a connector-based fluid isolation component; other configurations of this principle are contemplated.

Figure 19A:
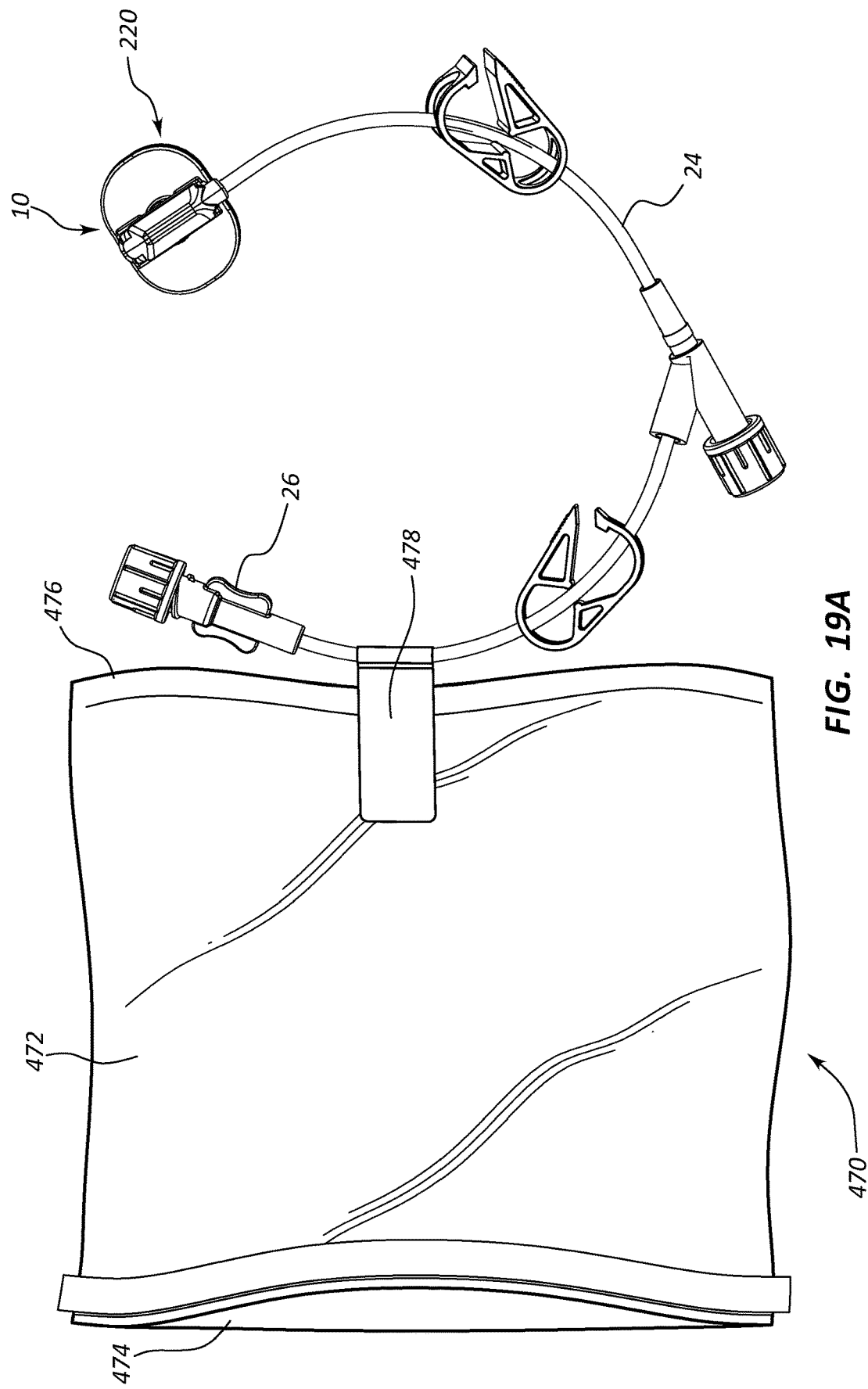
FIGS. 19A and 19B show various views of a fluid isolation component together with an infusion set, according to one embodiment.
Figure 19B:
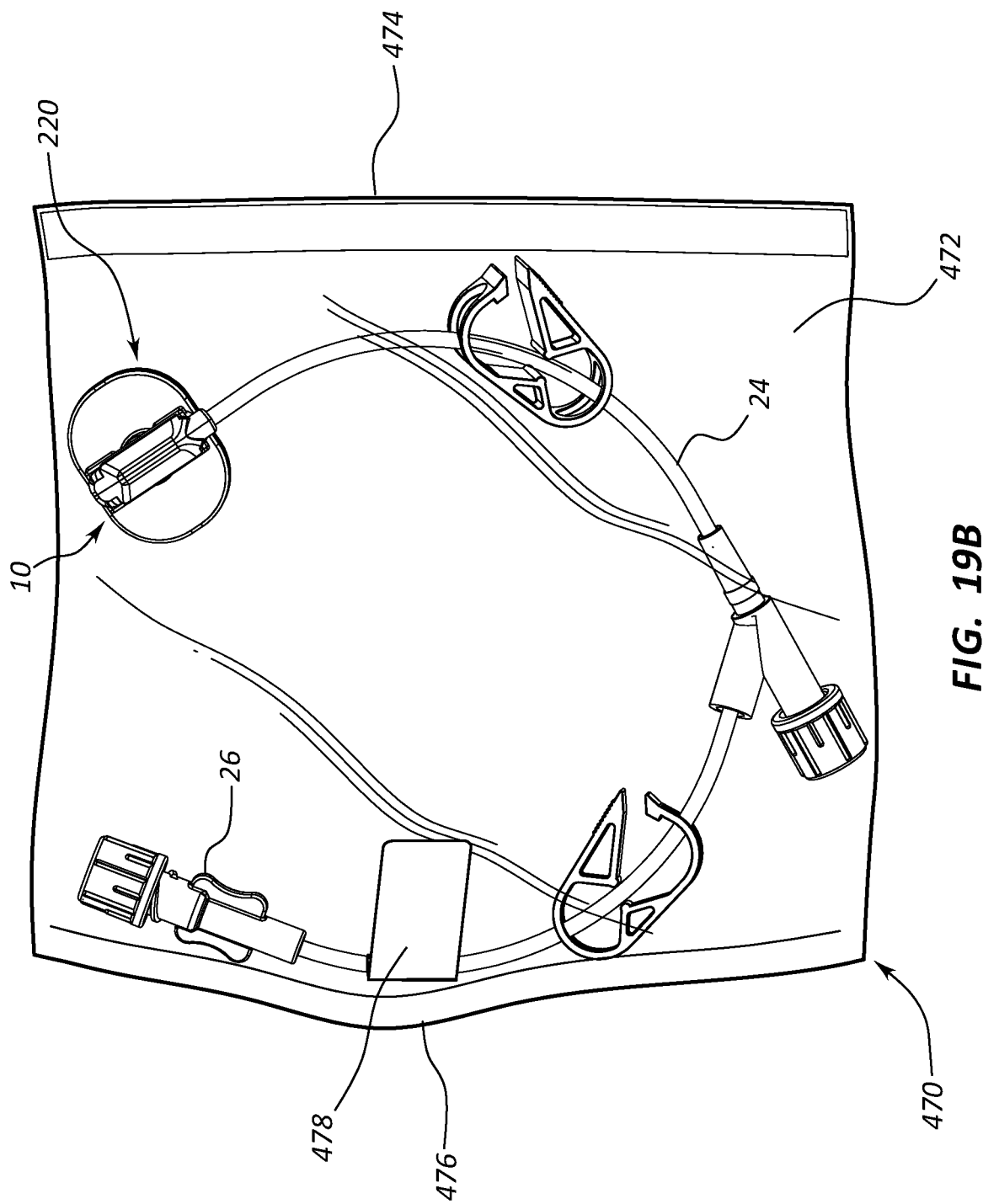

FIGS. 19A and 19B depict another example of a fluid isolation component for preventing unintended contact with fluid or vapors resulting from use of an infusion set. In particular, an infusion set 10 is shown, including a needle assembly 220, extension leg tubing 24, and luer connector 26. Also shown is a fluid isolation component 470, which in the present embodiment includes a bag 472 of plastic or other substantially fluid-impermeable material. The bag includes a sealable open end 474 and a closed end 476. The bag 472 is attached to the tubing 24 of the infusion set 10 or other suitable component thereof via and adhesive strip 478 or other suitable connective apparatus.

The bag 472 is initially inside-out before use of the infusion set 10. Once use of the infusion set 10 has ended, the user reaches a hand through the open end 474 of the bag 472 and pulls the infusion set into the bag, turning the bag right side-out in the process. Once the infusion set 10 is fully within the bag 472, the open end 474 of the bag 472 is sealed, as seen in FIG. 19B, thus isolating the user from any fluids or vapors included on the needle assembly 220 or any other portion of the infusion set 10. Note that the bag can be configured in one or more sizes and shapes, can include one-time, resealable, or other suitable type of sealing mechanism, and can be included with the infusion set in a variety of ways, both attached and detached thereto. The bag in the present embodiment is transparent, though in other embodiments it need not be.

Figure 20:
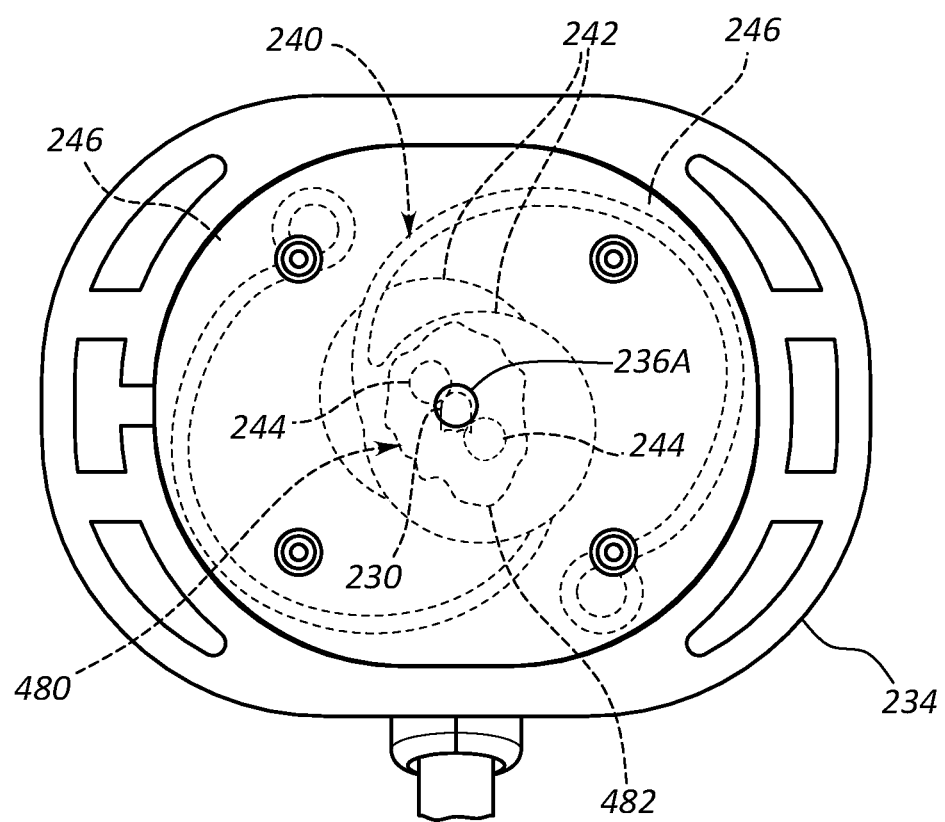
FIG. 20 is a bottom view of a safety needle assembly including a fluid isolation component according to one embodiment.

FIG. 20 depicts details of another possible fluid isolation component for use with the needle assembly 220 (shown in FIGS. 11-12B), or another suitable needle assembly. In particular, a fluid isolation component 480 is disclosed, including an amount of suitable viscous oil 482, such as silicone oil, interposed as a film between the shutters 242. When the needle 230 is retracted from the hole 236A in the needle assembly base 236, which retraction causes the shutters 242 to slide over and cover the hole, the oil 482 produces a fluid impermeable barrier layer between the shutters, thus preventing any fluid/vapor escaping the needle from escaping past the shutters. In other embodiments, other barriers can be employed between the shutters, including a gasket, O-ring, other compliant/elastomeric member, etc.

FIGS. 21A-24 depict various details regarding a fluid isolation component according to yet another embodiment, for use with a safety needle assembly. As will be described, the fluid isolation component in the present embodiment includes a self-sealing pad that prevents unintended leakage of fluids (e.g., liquids, gases) from the needle after use of the needle assembly. The self-sealing pad thus prevents undesired exposure to clinicians of potentially hazardous substances.

Figure 21A:
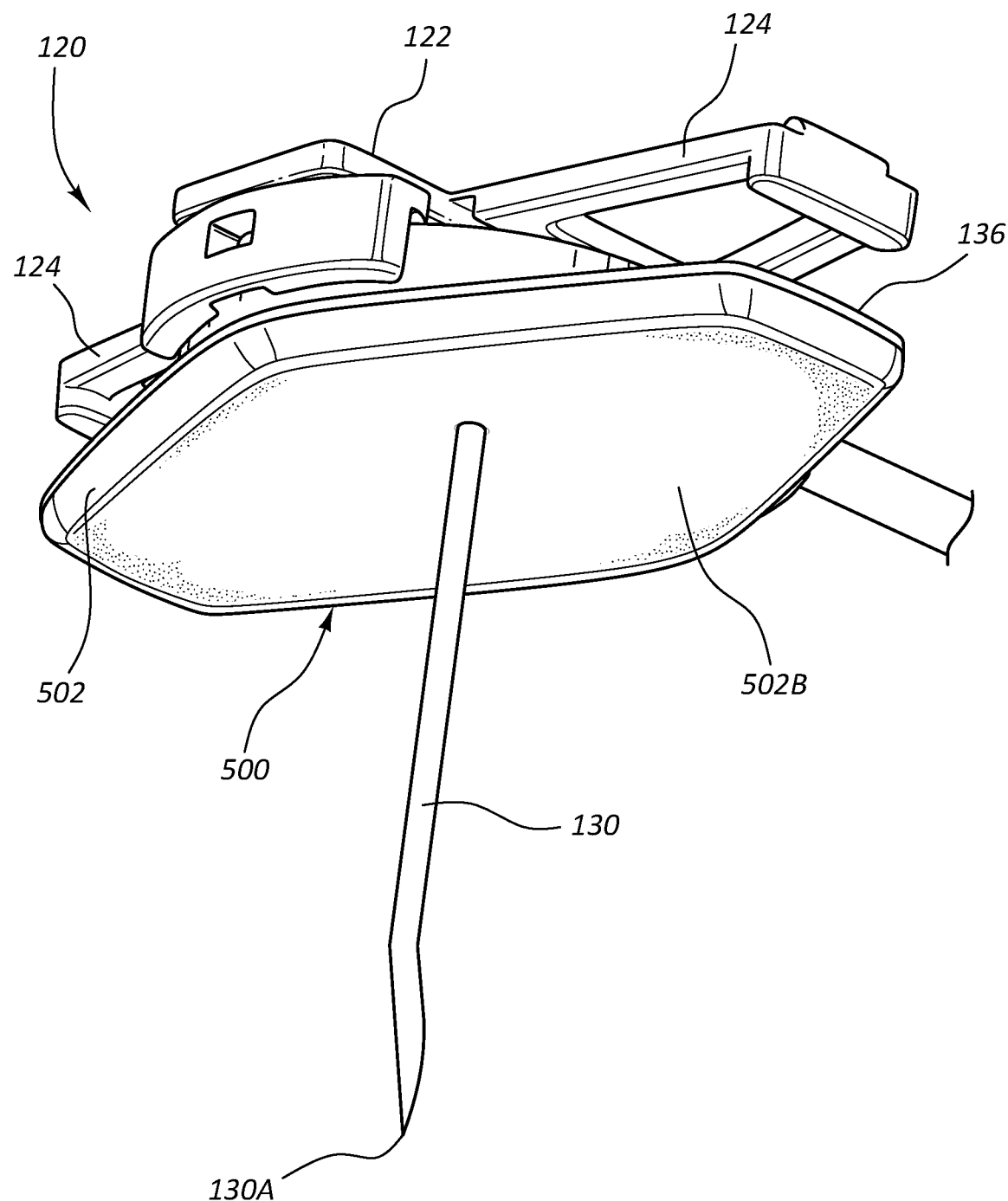
FIGS. 21A and 21B are various views of a needle assembly including a self-sealing pad according to one embodiment.
Figure 21B:
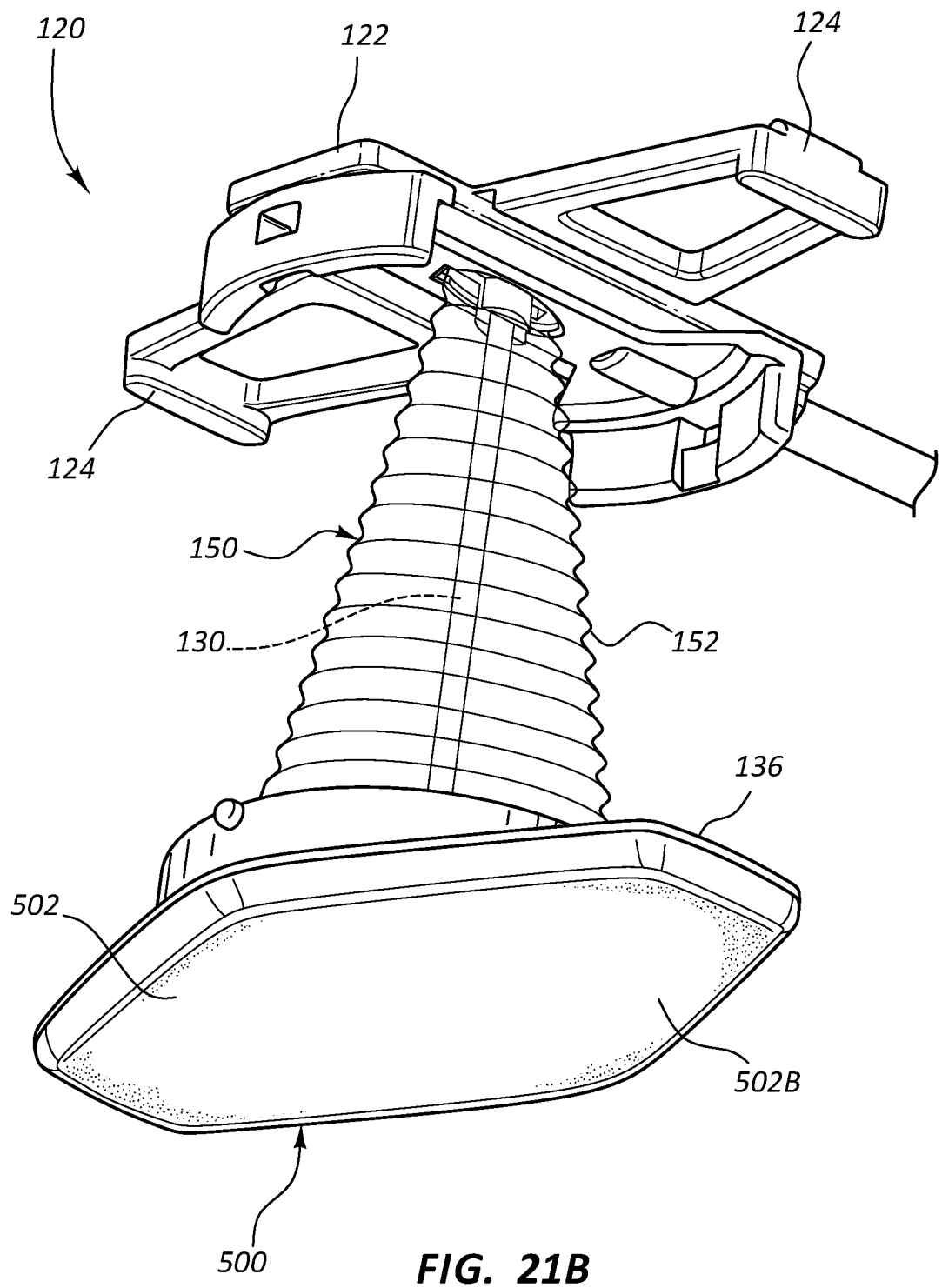

FIGS. 21A and 21B show the needle assembly 120 in similar configuration to that described further above in connection with FIGS. 5-6C. As before, the needle assembly 120 includes a first needle assembly portion, i.e., the handle portion 122, with handles 124 extending therefrom. The hollow needle 130 extends from the handle portion 122 and initially through the safety assembly 134 that is slidably disposed with respect to the needle 130 so as to be axially slidable therewith. The safety assembly 134 includes the base, also referred to herein as a second needle assembly portion or the base portion 136, which houses the needle safety component 140 (FIGS. 8A, 8B) for shielding the distal tip 130A of the needle 130 when use of the needle assembly is complete.

As already described further above, the needle assembly 120 further includes a first fluid isolation component 150 for isolating any fluid or vapor that may unintentionally escape from the needle 130 during use of the needle assembly. Specifically, the first fluid isolation component 150 includes the conically shaped, extensible shroud 152 disposed about the body of the needle 130 and extending between the handle portion 122 and the axially slidable safety assembly 134 of the base portion 136. The shroud 152 forms a hollow cone about the needle 130 and is corrugated with corrugations 154 in a bellows-like manner to enable it to fold up compactly when the safety assembly 134 is undeployed (FIG. 4) and to extend to cover and substantially encompass the needle 30 when the safety assembly 134 is deployed (FIG. 5). As already discussed. in the extended state shown in FIGS. 5 and 6C, the shroud 152 assists in isolating fluids/vapors present on the needle 130 or emitted from the needle distal tip 130A from contact with the clinician.

FIGS. 21A-21B further show a self-sealing pad 500 disposed on a bottom external surface of the base portion 136. The pad 500 includes a self-sealing material that enables the needle 130 to extend therethrough, as seen in FIG. 21A (also referred to as the first needle position), but seals when the needle is retracted back through the pad via separation of the base portion 136 from the handle portion 122, as seen in FIG. 21B (also referred to as the second needle position). In particular, and as shown in FIG. 21B, the full extension of the base portion 136 from the handle portion 122 causes the distal tip 130A of the needle 130 to be drawn through the pad 500 such that the distal tip is shielded within the base portion, in particular, shielded by the needle safety component 140. Because of its self-sealing characteristics, the pad 500 substantially seals the hole through which the needle 130 was disposed during needle assembly use, thus preventing any fluid leakage from the distal opening of the needle 130 to escape the base portion 136, as desired. Note that, though shown and described herein in connection with the needle assembly 120, the self-sealing pad 500 can be included with needle assemblies and infusion sets of a variety of configurations in addition to those discussed herein.

Figure 22A:
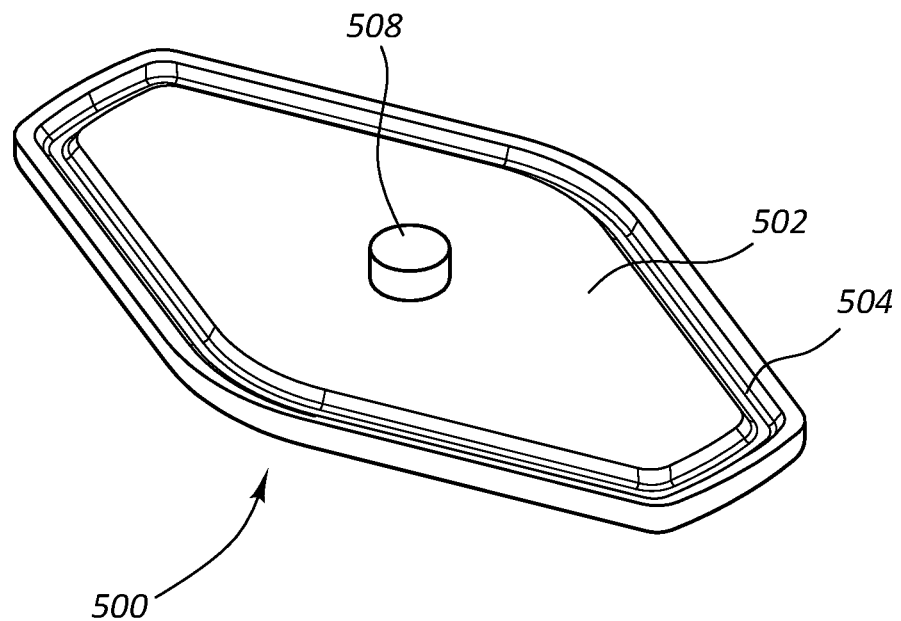
FIGS. 22A and 22B are various views of the self-sealing pad of FIGS. 21A and 21B.
Figure 22B:
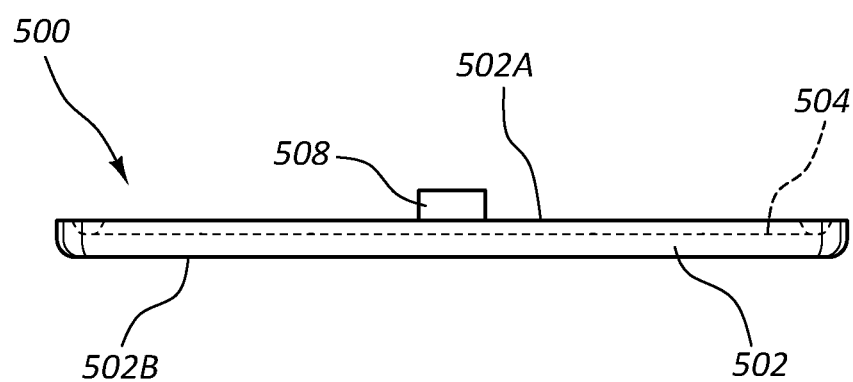

FIGS. 22A and 22B depict various features of the self-sealing pad 500 according to the present embodiment. As shown, the pad 500 includes a body 502 shaped to conform to the shape of the base 136, though in other embodiments the pad could include other shaped configurations. The body 502 defines an upper surface 502A that is configured to mate with the base portion 136 and a bottom surface 502B that serves as a skin-contacting surface for the needle assembly 120.

A groove 504 is defined about the perimeter and configured in the present embodiment to receive therein a corresponding protruded surface 506 defined on a bottom surface of the base portion 136. The receipt of the protruded surface 506 by the groove 504 assists in maintaining engagement of the pad 500 with the base portion 136, in one embodiment. The pad 500 can be affixed to the base portion 136 via a suitable adhesive or by other suitable methods, including mechanical fixation.

In one embodiment, the pad 500 includes silicone, though other self-sealing materials, plastics, and elastomers can be employed. In one embodiment, a liquid silicone rubber ("LSR") that is injection molded then cured is employed to form the pad 500. So configured, the skin-contacting bottom surface 502B of the pad 500 provides a compliant surface to rest against the skin of the patient during use of the needle assembly 120.

The pad body 502 further defines a centrally disposed raised portion 508, best seen in FIGS. 22A and 22B, which is shaped so as to compressively fit within an opening 136A that is defined in the base portion 136. As shown in FIGS. 23A and 23B, the raised portion 508 of the pad 500 is disposed within the opening 136A and is partially maintained in place via a compressive fit with the opening. So configured, the raised portion 508 acts as a septum to provide a robust fluid barrier when the needle 130 is withdrawn therethrough and shielded by the safety assembly 134, which occurs when the base portion 136 is selectively extended from the handle portion 122, as shown in FIG. 23B. Indeed, compression of the raised portion 508 by the opening 136A assists in the self-sealing characteristics of the pad 500 when the needle 130 is retracted, in one embodiment. Thus, the self-sealing pad 500 serves as a second fluid isolation component, together with the shroud 152, for preventing fluid/vapor escape from the needle assembly. The shape and size of both the raised portion and the opening can vary from what is shown and described herein. In the present embodiment, the distal tip 130A of the needle 130 fully withdraws from the raised portion 508, though in other embodiments the distal tip can remain in the raised portion 508 after shielding thereof by the safety assembly. An example of the latter configuration would include the distal tip of the needle retracting fully from the lower surface 502B of the pad body while still residing within raised portion 508 of the pad.

Figure 24:
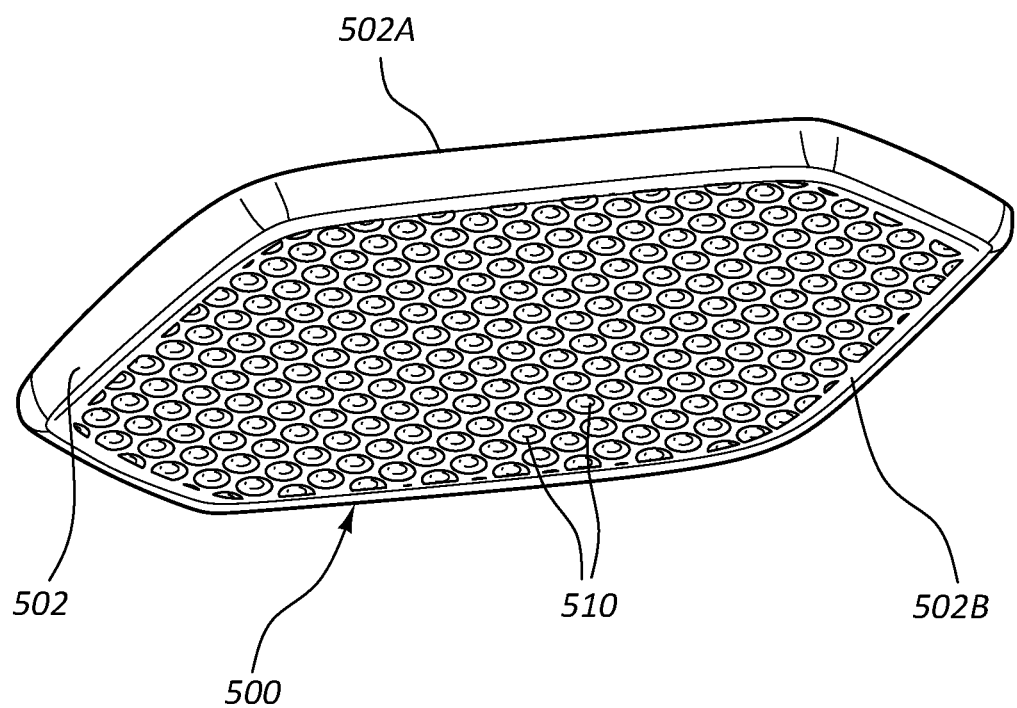
FIG. 24 is a perspective view of a self-sealing pad according to one embodiment.

The self-sealing pad can be configured in other ways. For instance, FIG. 24 shows the bottom surface 502B as including a plurality of texture features 510 for increasing patient comfort while the needle assembly 120 is disposed on the skin of the patient. Also, in one embodiment, it is appreciated that the self-sealing pad can be treated so as to offer antimicrobial/antibacterial properties. Further, in one embodiment, the bottom surface of the self-sealing pad can include an adhesive material to enable the pad to act as a securement device in maintaining the infusion set in place at a desired position on the patient's skin during use of the needle assembly. It is further appreciated that the needle assembly and accompanying infusion set can include one of many possible shapes, sizes, and configurations in addition to those shown and discussed herein.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A needle assembly, comprising:
   a handle portion, comprising:
      a needle having a proximal end secured in the handle portion and a distal end extending from the handle portion; and
      an extension tube secured in the handle portion to establish fluid communication with a lumen of the needle;
   a base portion releasably coupled to the handle portion in a needle assembly use configuration, the base portion comprising:

a bottom external surface having an opening;
a safety assembly including a needle safety component; and
a self-sealing pad covering the bottom external surface, the self-sealing pad comprising:
an antimicrobial component;
an upper surface designed to mate with the base portion;
a raised portion compressively positioned in the opening of the bottom external surface; and
a skin-contacting surface,
wherein the needle assembly is configured to be placed on skin such that the needle passes through the self-sealing pad and the skin.

2. The needle assembly according to claim 1, further comprising a fluid isolation component positioned between the self-sealing pad and the handle portion.

3. The needle assembly according to claim 2, wherein the fluid isolation component is an extensible shroud having a proximal end connected to the handle portion and distal portion connected to the base portion, wherein the extensible shroud surrounds an entire length of the needle extending from the handle portion in a needle assembly safety configuration.

4. The needle assembly according to claim 3, wherein the extensible shroud is corrugated, including a plurality of corrugations designed to compactly fold in the needle assembly use configuration.

5. The needle assembly according to claim 4, wherein the extensible shroud is formed from an impermeable material.

6. The needle assembly according to claim 3, wherein the extensible shroud includes a plurality of interlocked, telescoping segments.

7. The needle assembly according to claim 1, wherein the base portion is releasable from the handle portion to permit translation from the needle assembly use position to a needle assembly safety position, and wherein a distal tip of the needle contacts the needle safety component in the needle assembly safety position.

8. The needle assembly according to claim 7, wherein the needle safety component comprises a spring-based obstruction biased to obstruct the opening of the bottom external surface of the base portion in the needle assembly safety position.

9. The needle assembly according to claim 8, wherein the spring-based obstruction includes at least one shutter having a distal end designed to obstruct the opening of the bottom external surface, a proximal end coupled to the base portion, and a spring arm connecting the proximal end to the distal end.

10. The needle assembly according to claim 9, further comprising a fluid isolation component comprising an absorbent pad disposed on the at least one shutter, the distal tip of the needle resting against the absorbent pad in the needle assembly safety position.

11. The needle assembly according to claim 1, wherein the skin-contacting surface of the self-sealing pad includes a plurality of texture features designed to increase patient comfort.

12. The needle assembly according to claim 1, wherein the skin-contacting surface includes an adhesive designed to prevent movement of the needle assembly during use.

13. The needle assembly according to claim 1, wherein the antimicrobial component is disposed on the skin-contacting surface of the self-sealing pad.

14. The needle assembly according to claim 1, wherein the self-sealing pad is formed from liquid silicone rubber.

15. The needle assembly according to claim 1, wherein the base portion is releasable from the handle portion to permit translation from the needle assembly use position to a needle assembly safety position, and wherein a distal tip of the needle is within the raised portion of the self-sealing pad in the needle assembly safety position.

\* \* \* \* \*